(12) United States Patent
Yin et al.

(10) Patent No.: US 12,396,962 B2
(45) Date of Patent: *Aug. 26, 2025

(54) NANOPARTICLES CONTAINING A TAXANE AND THEIR USE

(71) Applicant: Fulgent Genetics, Inc., El Monte, CA (US)

(72) Inventors: Ray Yin, Wilmington, DE (US); Jing Pan, Newark, DE (US); Yubei Zhang, Hockessin, DE (US); Bingsen Zhou, West Covina, CA (US); Yun Yen, Arcadia, CA (US)

(73) Assignee: Fulgent Genetics, Inc., El Monte, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 18/239,715

(22) Filed: Aug. 29, 2023

(65) Prior Publication Data
US 2024/0108586 A1    Apr. 4, 2024

Related U.S. Application Data

(63) Continuation of application No. 17/184,977, filed on Feb. 25, 2021, now Pat. No. 11,801,230, which is a
(Continued)

(51) Int. Cl.
*A61K 9/19*    (2006.01)
*A61K 9/00*    (2006.01)
(Continued)

(52) U.S. Cl.
CPC .......... *A61K 9/5146* (2013.01); *A61K 9/0019* (2013.01); *A61K 9/19* (2013.01);
(Continued)

(58) Field of Classification Search
CPC ...... A61K 9/5146; A61K 9/0019; A61K 9/19; A61K 9/513; A61K 31/337; B82Y 5/00
See application file for complete search history.

(56) References Cited

U.S. PATENT DOCUMENTS

| 5,919,442 A | 7/1999 | Dendritech |
|---|---|---|
| 6,177,414 B1 | 1/2001 | Tomalia et al. |

(Continued)

FOREIGN PATENT DOCUMENTS

| WO | 0149268 | 7/2001 | |
|---|---|---|---|
| WO | WO-2012094620 A2 * | 7/2012 | ........... A61K 31/337 |

OTHER PUBLICATIONS

Abumanhal-Masarweh, Hanan, et al. "Sodium bicarbonate nanoparticles modulate the tumor pH and enhance the cellular uptake of doxorubicin." Journal of Controlled Release 296 (Feb. 2019): 1-13.
(Continued)

*Primary Examiner* — Ernst V Arnold
(74) *Attorney, Agent, or Firm* — Greenberg Traurig, LLP

(57) ABSTRACT

Symmetrically and asymmetrically branched homopolymers are modified at the surface level with functional groups that enable forming aggregates with a taxane, such as, paclitaxel and derivatives thereof, which are water insoluble or poorly water soluble. The aggregates are formed by interaction of a taxane and a homopolymer. Such aggregates improve drug solubility, stability, delivery and efficacy.

20 Claims, 24 Drawing Sheets

Related U.S. Application Data continuation of application No. 16/041,821, filed on Jul. 22, 2018, now abandoned, which is a continuation-in-part of application No. 15/430,508, filed on Feb. 12, 2017, now abandoned, which is a continuation of application No. 14/765,344, filed as application No. PCT/US2014/014336 on Feb. 1, 2014, now abandoned.

(60) Provisional application No. 61/760,890, filed on Feb. 5, 2013.

(51) Int. Cl.
*A61K 9/51* (2006.01)
*A61K 31/337* (2006.01)
*A61P 35/00* (2006.01)
*B82Y 5/00* (2011.01)

(52) U.S. Cl.
CPC ............ *A61K 9/513* (2013.01); *A61K 31/337* (2013.01); *B82Y 5/00* (2013.01)

(56) References Cited

U.S. PATENT DOCUMENTS

| | | | |
|---|---|---|---|
| 7,754,500 | B2 | 7/2010 | Yin et al. |
| 11,801,230 | B2 * | 10/2023 | Yin ..................... A61K 9/5146 |
| 2002/0013430 | A1 | 1/2002 | Klaerner et al. |
| 2002/0041898 | A1 | 4/2002 | Imarx |
| 2003/0187178 | A1 | 10/2003 | Kohlstruk et al. |
| 2004/0009229 | A1 | 1/2004 | Unger et al. |
| 2006/0041058 | A1 | 2/2006 | Yin et al. |
| 2006/0051315 | A1 | 3/2006 | Scaria et al. |
| 2006/0127350 | A1 | 6/2006 | Heegaard et al. |
| 2007/0128118 | A1 | 6/2007 | Yu |
| 2008/0114077 | A1 | 5/2008 | Yin et al. |
| 2011/0060036 | A1 | 3/2011 | Nie et al. |
| 2014/0314664 | A1 | 10/2014 | Qin et al. |
| 2014/0328918 | A1 | 11/2014 | Fetzer |
| 2018/0235884 | A1 | 8/2018 | Qin |
| 2018/0326081 | A1 | 11/2018 | Owen |
| 2019/0262460 | A1 | 8/2019 | Shinde |
| 2020/0113877 | A1 | 4/2020 | Shinde |
| 2020/0206356 | A1 | 7/2020 | Alargova |

OTHER PUBLICATIONS

ClinicalTrials.gov FID-007 in Treating Participants with Advanced Solid Tumors, May 25, 2018.
Guillerm, B., et al., "Novel Investigations on Kinetics and Polymerization Mechanism of Oxazolines Initiated by Iodine" Macromolecules, 43, 5964-5970, Jul. 2010, 10.1021/ma1009808.
Rapp RP, Bivins BA, "Final in-line filtration: removal of contaminants from IV fluids and drugs" Hosp Formul, Dec. 1983; 18:1124-1128 Abstract only.
Reddy, L. Harivardhan, and Didier Bazile. "Drug delivery design for intravenous route with integrated physicochemistry, pharmacokinetics and pharmacodynamics: illustration with the case of taxane therapeutics." Advanced Drug Delivery Reviews 71 (May 2014): 34-57.
Thomas, J. S., et al., "A phase 1 trial of FID-007, a novel nanoparticle paclitaxel formulation, in patients with solid tumors", Journal of Clinical Oncology 39, No. 15_suppl (May 20, 2021) 3021-3021.
Thomas, J., et al., "A Phase 1 Trial of FID-007, a Novel Nanoparticle Paclitaxel Formulation, in Patients with Solid Tumors" https://classic.clinicaltrials.gov/ct2/show/NCT03537690, 1 page, May 5, 2021.
International Search Report issued Jun. 21, 2022 in International Application No. PCT/US22/16368.
D'Emanuele et al., "Dendrimer-drug interaction," Adv Drug Del News57, 2147-2162, 2005.
Wolinsky et al., "Therapeutic . . . treatment," Adv Drug Del Rev 60, 1037-1055, 2008.
Cheng et al., "New insight . . . aggregates," J Phys Chem B, 113, 8339-8346, 2009.
Gillies et al., "pH-Responsive . . . doxorubicin," Bioconjugate Chem 16,361-368, 2005.
Tan et al., "Aggregation . . . dendrimer," Eur Phy J E 27:205-211, 2008.
Hoogenboom, "Poly . . . Applications," Ang Chem Inter Ed 48:7978-7994, 2009.
Lee et al., J Controlled Release 89:437-446, 2003.
"Microstructure . . . Cryo-SEM 2007," ProQuest, p. 127.

* cited by examiner

Dendrimers

Dendrigrafts

Regular Comb-branches

Star-branched

Polypropyleneimine Dendrimer-4

Polypropyleneimine Dendrimer-8

Random ABP					Regular ABP

Polymer and polymer-drug aggregates with the polymer concentration at 25 mg/mL in saline

NANOPARTICLES CONTAINING A TAXANE AND THEIR USE

CROSS REFERENCE

The instant application is a continuation-in-part of U.S. Ser. No. 15/430,508 filed on Feb. 12, 2017, which is a continuation of U.S. Ser. No. 14/765,344 filed on Aug. 2, 2015, which is a 371 national stage application of PCT Ser. No. US14/14336 filed on Feb. 1, 2014, which claims benefit of U.S. Ser. No. 61/760,890, which was filed on Feb. 5, 2013.

FIELD OF THE INVENTION

The present disclosure relates to a surface-modified branched polymer (MBP) or a linear polymer, which can either be a surface-modified symmetrically branched polymer (SBP); a surface-modified asymmetrically branched polymer (ABP); or a linear polymer with at least one chain end modified with a hydrophobic group, which on exposure to a water insoluble or poorly water soluble taxane forms a composite nanoparticle or nanoaggregate, wherein the drug is dispersed or deposited at or near hydrophobic domains, such as, at the surface or at structures where hydrophobic portions, segments or sites are located. The particles or aggregates of interest are stable, for example, can be desiccated and rehydrated. The nanoparticles or nanoaggregates can range from about 20 nm to about 500 nm in diameter. Hydrophobic, electrostatic, metal-ligand interactions, hydrogen bonding and other molecular interactions may be involved in the spontaneous interactions between the water insoluble or poorly water soluble taxane and the homopolymer to form aggregates. The particles or aggregates of interest have a controlled release profile and thus find utility, for example, as a carrier for the controlled release of a taxane in a host for treating a suitable disorder; and the like. For example, the present disclosure relates to the use of such polymers for the in vivo delivery of a taxane, such as, paclitaxel and derivatives thereof, with lower toxicity, improved solubility, greater bioavailability and enhanced efficacy in treating cancers.

BACKGROUND

Symmetrically Branched Polymers

A new class of polymers called dendritic polymers, including Starburst dendrimers (or Dense Star polymers) and Combburst dendrigrafts (or hyper comb-branched polymers), recently was developed and studied for various industrial applications. Those polymers often possess: (a) a well-defined core molecule, (b) at least two concentric dendritic layers (generations) with symmetrical (equal length) branches and branch junctures and (c) exterior surface groups, such as. polyamidoamine (PAMAM)-based branched polymers and dendrimers described in U.S. Pat. Nos. 4,435,548; 4,507,466; 4,568,737; 4,587,329; 5,338,532; 5,527,524; and 5,714,166. Other examples include polyethyleneimine (PEI) dendrimers, such as those disclosed in U.S. Pat. No. 4,631,337; polypropyleneimine (PPI) dendrimers, such as those disclosed in U.S. Pat. Nos. 5,530,092; 5,610,268; and 5,698,662; Frechet-type polyether and polyester dendrimers, core shell tectodendrimers and others, as described, for example, in, "Dendritic Molecules," edited by Newkome et al., VCH Weinheim, 1996, "Dendrimers and Other Dendritic Polymers," edited by Frechet & Tomalia, John Wiley & Sons, Ltd., 2001; and U.S. Pat. No. 7,754,500.

Combburst dendrigrafts are constructed with a core molecule and concentric layers with symmetrical branches through a stepwise synthetic method. In contrast to dendrimers, Combburst dendrigrafts or polymers are generated with monodisperse linear polymeric building blocks (U.S. Pat. Nos. 5,773,527; 5,631,329 and 5,919,442). Moreover, the branch pattern is different from that of dendrimers. For example, Combburst dendrigrafts form branch junctures along the polymeric backbones (chain branches), while Starburst dendrimers often branch at the termini (terminal branches). Due to the living polymerization techniques used, the molecular weight distributions (Mw/Mn) of those polymers (core and branches) often are narrow. Thus, Combburst dendrigrafts produced through a graft-on-graft process are well defined with Mw/Mn ratios often approaching 1.

SBP's, such as dendrimers, are produced predominantly by repetitive protecting and deprotecting procedures through either a divergent or a convergent synthetic approach. Since dendrimers utilize small molecules as building blocks for the cores and the branches, the molecular weight distribution of the dendrimers often is defined. In the ease of lower generations, a single molecular weight dendrimer often is obtained. While dendrimers often utilize small molecule monomers as building blocks, dendrigrafts use linear polymers as building blocks.

In addition to dendrimers and dendrigrafts, other SBP's include symmetrical star-shaped or comb-shaped polymers, such as, symmetrical star-shaped or comb-shaped polyethyleneoxide (PEO), polyethyleneglycol (PEG), PEI, PPI, polyoxazoline (PDX), polymethyloxazoline (PMOX), polyethyloxazoline (PEOX), polystyrene, polymethylmethacrylate, polydimethylsiloxane or a combination thereof.

Asymmetrically Branched Polymers

Unlike SBP's, asymmetrically branched polymers (ABP), particularly asymmetrically branched dendrimers or regular ABP (reg-ABP), often possess a core, controlled and well-defined asymmetrical (unequal length) branches and asymmetrical branch junctures as described in U.S. Pat. Nos. 4,289,872; 4,360,646; and 4,410,688.

On the other hand, a random ABP (ran-ABP) possesses: a) no core, b) functional, groups both at the exterior and in the interior, c) random/variable branch lengths and patterns (i.e., termini and chain branches), and d) unevenly distributed interior void spaces.

The synthesis and mechanisms of ran-ABP's, such as those made from PEI, were reported by Jones et al., J. Org. Chem. 9, 125 (1944), Jones et al., J. Org. Chem. 30, 1994 (1965) and Dick et al., J. Macromol. Sci. Chem., A4 (6), 1301-1314, (1970)). Ran-ABP, such as those made of PDX, i.e., poly(2-methyloxazoline) and poly(2-ethyloxazoline), was reported by Litt (J. Macromol. Sci. Chem. A9(5), 703-727 (1975)) and Warakomski (J. Polym. Sci. Polym. Chem. 28, 3551 (1990)). The synthesis of ran-ABP's often can involve a one-pot divergent or a one-pot convergent method.

Homopolymers

A homopolymer can relate to a polymer or to a polymer backbone composed of the same repeat unit, that is, the homopolymer is generated from the same monomer (e.g., PEI linear polymers, PDX linear polymers, PEI dendrimers, polyamidoamine (PAA) dendrimers or PDX dendrigrafts and randomly ranched polymers). The monomer can be a simple compound or a complex or an assemblage of compounds where the assemblage or complex is the repeat unit in the homopolymer. Thus, if an assemblage is composed of three compounds, A, B and C; the complex can be depicted as ABC. On the other hand, a polymer composed of (ABC)-

(ABC)-(ABC) . . . , is a homopolymer for the purposes of the instant disclosure. The homopolymer may be linear or branched. Thus, in the case of a randomly branched PEI, although there are branches of different length and branches occur randomly, that molecule is a homopolymer for the purposes of the instant disclosure because that branched polymer is composed of a single monomer, the ethylene-imine or aziridine repeat unit. Also, one or more of the monomer or complex monomer components can be modified, substituted, derivatized and so on, for example, modified to carry a functional group. Such molecules are homopolymers for the purposes of the instant disclosure as the backbone is composed of a single simple or complex monomer.

Poorly Water Soluble Drugs: Taxanes

Paclitaxel is a water insoluble drug sold as TAXOL® by Bristol-Myers Squibb. Paclitaxel is derived from the Pacific Yew tree, *Taxus brevifolia* (Wan et al., J. Am. Chem. Soc. 93:2325, 1971). Taxanes, including paclitaxel and docetaxel (also sold as TAXOTERE® under registered trademark of Aventis Pharma S.A., FR), are used to treat various cancers, including, breast, ovarian and lung cancers, as well as colon, and head and neck cancers, etc.

However, the poor aqueous solubility of paclitaxel has hampered the widespread use thereof. Currently, TAXOL® and generics thereof are formulated using a 1:1 solution of ethanol:CREMAPHOR® (polyethyoxylated castor oil, registered trademark of BASF, DE) to solubilize the drug. The presence of CREMAPHOR® has been linked to severe hypersensitivity reactions and consequently requires medication of patients with corticosteroids (e.g., dexamethasone) and antihistamines.

Alternatively, conjugated paclitaxel, for example, ABRAXANE® (under registered trademark of Abraxis Bioscience, NJ, USA), which is produced by mixing paclitaxel with human serum albumin, has eliminated the need for corticosteroids and antihistamine injections. However, ABRAXANE® generates undesirable side effects, such as, severe cardiovascular events, including chest pain, cardiac arrest, supraventricular tachycardia, edema, thrombosis, pulmonary thromboembolism, pulmonary emboli, hypertension etc., which prevents patients with high cardiovascular risk from using the drug.

Delivery of Poorly Water Soluble Drugs

Although branched polymers, including SBP's and ABP's, have been used for drug delivery, those attempts are focused primarily on the chemical attachment of the drug to the polymer, or physical encapsulation of such drugs in the interior through unimolecular encapsulation (U.S. Pat. Nos. 5,773,527; 5,631,329; 5,919,442; and 6,716,450).

For example, dendrimers and dendrigrafts are believed to entrap physically bioactive molecules using unimolecular encapsulation approaches, as described in U.S. Pat. Nos. 5,338,532; 5,527,524; and 5,714,166 for dense star polymers, and U.S. Pat. No. 5,919,442 for hyper comb-branched polymers. Similarly, the unimolecular encapsulation of various drugs using SBP's to form a, "dendrimer box," was reported in Tomalia et al., Angew. Chem. Int. Ed. Engl., 1990, 29, 138, and in, "Dendrimers and Other Dendritic Polymers," edited by Frechet & Tomalia, John Wiley & Sons, Ltd., 2001, pp. 387-424.

Branched core shell polymers with a hydrophobic core and a hydrophilic shell may be used to entrap a poorly water soluble drug through molecular encapsulation. Randomly branched and hyperbranched core shell structures with a hydrophilic core and a hydrophobic shell have also been used to carry a drug through unimolecular encapsulation and pre-formed nanomicelles (U.S. Pat. No. 6,716,450 and Liu et al., Biomaterials 2010, 10, 1334-1341). However, those unimolecular and pre-formed micelle structures are generated in the absence of a drug.

In embodiments, block copolymers, such as, miktoarm polymers (i.e., Y shaped/$AB_2$-type star polymers) and linear (A)-dendritic (B) block copolymers, were observed to form stereocomplexes with paclitaxel (Nederberg et al., Biomacromolecules 2009, 10, 1460-1468 and Luo et al., Bioconjugate Chem. 2010, 21, 1216). Those block copolymers closely resemble traditional lipid or AB-type linear block copolymers, which are well known surfactants used for the generation of micelles.

However, such branched block copolymers are difficult to make and thus, are not suitable for mass production.

There is no description of modifying branched or linear homopolymers with a hydrophobic group, which on exposure to a poorly soluble or water insoluble drug, spontaneously form stable aggregates which are suitable for controlled drug delivery.

SUMMARY

The present invention is directed to an aggregate comprising:

a) a polyoxazoline comprising at least one first terminal group modified with a hydrophobic moiety, wherein the polyoxazoline further comprises a linear portion, a branched portion or both, and the branched portion comprises a symmetrically branched polymer, an asymmetrically branched polymer or a combination thereof; and the polyoxazoline comprises a molar ratio of monomer to initiator in a range of, for example, from 50:1 to 80:1, and b) a taxane, wherein the polyoxazoline and the taxane has a weight ratio of polymer to taxane of, for example, 6:1 to 8:1, and the aggregate is from about 50 nm to about 100 nm in size, and wherein the aggregate has a filtration rate through a 0.22 µm filter in the range of from 50 to 100 percent.

In an aspect, the present disclosure is directed to use of modified branched polymers (MBP) or linear polymers to increase the solubility of taxanes, such as, paclitaxel, and derivatives thereof.

In an aspect of the disclosure, the asymmetrically branched polymer (ABP) has either random or regular, asymmetrical branches. The random ABP can also have a mixture of terminal and chain branching patterns.

In another aspect of the disclosure, both ABP's and SBP's can be modified further with at least one molecule or group capable of forming additional branches at a given time so that new material properties can be achieved, wherein additional functional groups further maybe attached. All of the modified polymers can be defined as modified SBP's or ABP's.

In another aspect of the disclosure, the unmodified and modified branched polymers either can be produced by a divergent or a convergent method, and either a stepwise or a one-step synthetic process can be used.

In another aspect of the disclosure, the SBP includes, but is not limited to, PAA dendrimers; PEI dendrimers; PPI dendrimers; polyether dendrimers; polyester dendrimers; comb-branched/star-branched polymers, such as, PAA, polyethyleneoxide (PEO), polyethyleneglycol (PEG), PMOX, PEOX, polymethylmethacrylate (PMA), polystyrene, polybutadiene, polyisoprene and polydimethylsiloxane; comb-branched dendrigrafts, such as, PEOX, PMOX, polypropyloxazoline (PPDX), polybutyloxazoline, PEI, PAA; and so on.

In a further aspect of the disclosure, the SBP can have an interior void space, while the ABP can have unevenly distributed void spaces.

In another aspect of the disclosure, a hybrid branched polymer comprising, the aforementioned SBP's, such as, dendrimers or dendrigrafts, and ABP's, such as, regular and randomly branched polymers, as well as star-branched and comb-branched polymers, or combination thereof, also can be used for the generation of said drug-induced aggregates or nanoparticles of interest.

In another aspect of the disclosure, the branched polymers are modified with functional groups, such as, but not limited to, $NH_2$, NHR, $NR_2$, $NR_3^+$, COOR, COOH, $COO^-$, OH, C(O)R, $C(O)NH_2$, C(O)NHR or $C(O)NR_2$, wherein R can be any aliphatic group, aromatic group or combination thereof; an aliphatic group (e.g., a hydrocarbon chain), which can be branched, can contain one or more double and/or triple bonds and/or may be substituted; an aromatic group, which may contain a plurality of rings, which may be fused or separated, the rings may be of varying size and/or may contain substituents; perfluorocarbon chains; saccharides and/or polysaccharides, which may be of varying ring sizes, the rings may contain a heteroatom, such as a sulfur or a nitrogen atom, may be substituted, may contain more than one species of saccharide, may be branched and/or may be substituted; polyethylene glycols; and the like.

The molecular weight of the MBP's can range from about 500 to over 5,000,000; from about 500 to about 1,000,000; from about 1,000 to about 500,000; from about 2,000 to about 100,000.

In another aspect of the disclosure, the surface of the SBP's and ABP's is modified so that the physical properties of the surface groups will be more compatible with a taxane, thus making taxane more miscible with the surface group region, domain, portion or segment of the MBP's.

In an embodiment, the modification of a branched polymer or a linear polymer at a chain end is with a hydrophobic functional group, such as, aliphatic chains (e.g., hydrocarbon chains comprising 1 to about 22 carbons, whether linear or branched), aromatic structures (e.g. containing one or more aromatic rings, which may be fused) or combinations thereof.

In contrast to known drug carriers, the branched or linear polymer structures of the instant invention do not physically entrap taxane within each polymer molecule. Instead, a taxane either can be located, at or dispersed in the domains/regions containing functional groups of each branched or linear polymer.

The resulting structures of interest optionally can be preserved, for example, by lyophilization or other form of desiccation, which may further stabilize the structures of interest. Once redissolved in water or a buffer, nanoparticles with sizes ranging from about 50 to about 500 nm in diameter can be obtained.

The presence of multiple, often functionalized branches enables the formation of intramolecular and intermolecular crosslinks, which may stabilize the taxane-containing nanoparticles. On dilution, said physical aggregate or nanoparticle deconstructs releasing drug at a controlled rate.

In another aspect of the disclosure, a mixture of linear and branched polymers also can be utilized to encapsulate a taxane. At least one end group of said linear and/or branched polymer is modified with a hydrophobic moiety or functional group. A hydrophobic moiety or functional group can include, but is not limited to, hydrocarbon chains (e.g., containing 1-22 carbons with either saturated or unsaturated chemical bonds) and hydrophobic groups containing aralkyl, aromatic rings, fluorocarbons etc.

In another aspect of the disclosure, the branched or linear polymer can comprise targeting moieties/groups including, but not limited to, an antibody or antigen-binding portion thereof, antigen, cognate carbohydrates (e.g., sialic acid), a cell surface receptor ligand, a moiety bound by a cell surface receptor, such as, a prostate-specific membrane antigen (PSMA), a moiety that binds a cell surface saccharide, an extracellular matrix ligand, a cytosolic receptor ligand, a growth factor, a cytokine, an incretin, a hormone, a lectin, a lectin, ligand, such as, a galactose, a galactose derivative, an N-acetylgalactosamine, a matmose, a mannose derivative and the like, a vitamin, such as, a folate or a biotin; avidin, streptavidin, neutravidin, DNA, RNA etc. Such targeted nanoparticles release drug at the preferred treatment locations, and therefore, enhance local effective concentrations and can minimize undesired side effects.

In another aspect of the disclosure, a targeting moiety/group and a functional group, including, hydrophobic, hydrophilic and/or ionic functional groups, are attached to the branched polymer prior to the formation of the composite nanoparticle for targeted drug delivery.

In another aspect of the disclosure, specific ranges of monomer:initiator and polymer:taxane ratios result in drug nanoparticles of appropriate size to facilitate large scale manufacturing of the drug nanoparticles, sterilization of drug nanoparticles, and result in improved drug efficacy as compared to other monomer:initiator and/or polymer:taxane ratios.

Additional features and advantages of the present disclosure are described in, and will be apparent from, the following Detailed Description and the attached Figures.

BRIEF DESCRIPTION OF THE FIGURES

The following description of the figures and the respective drawings are non-limiting examples that depict various embodiments that exemplify the present disclosure.

FIG. 6A presents chemical modification reactions of random asymmetrically branched PEI homopolymers. FIG. 6B depicts a one-pot synthesis of hydrophobically modified, randomly branched poly(2-ethyloxazoline) with a primary amino group at the focal point of the polymer. The initiator/surface group (I) is the brominated hydrocarbon. The reaction opens the oxazoline ring.

Figures 7A, 7B:
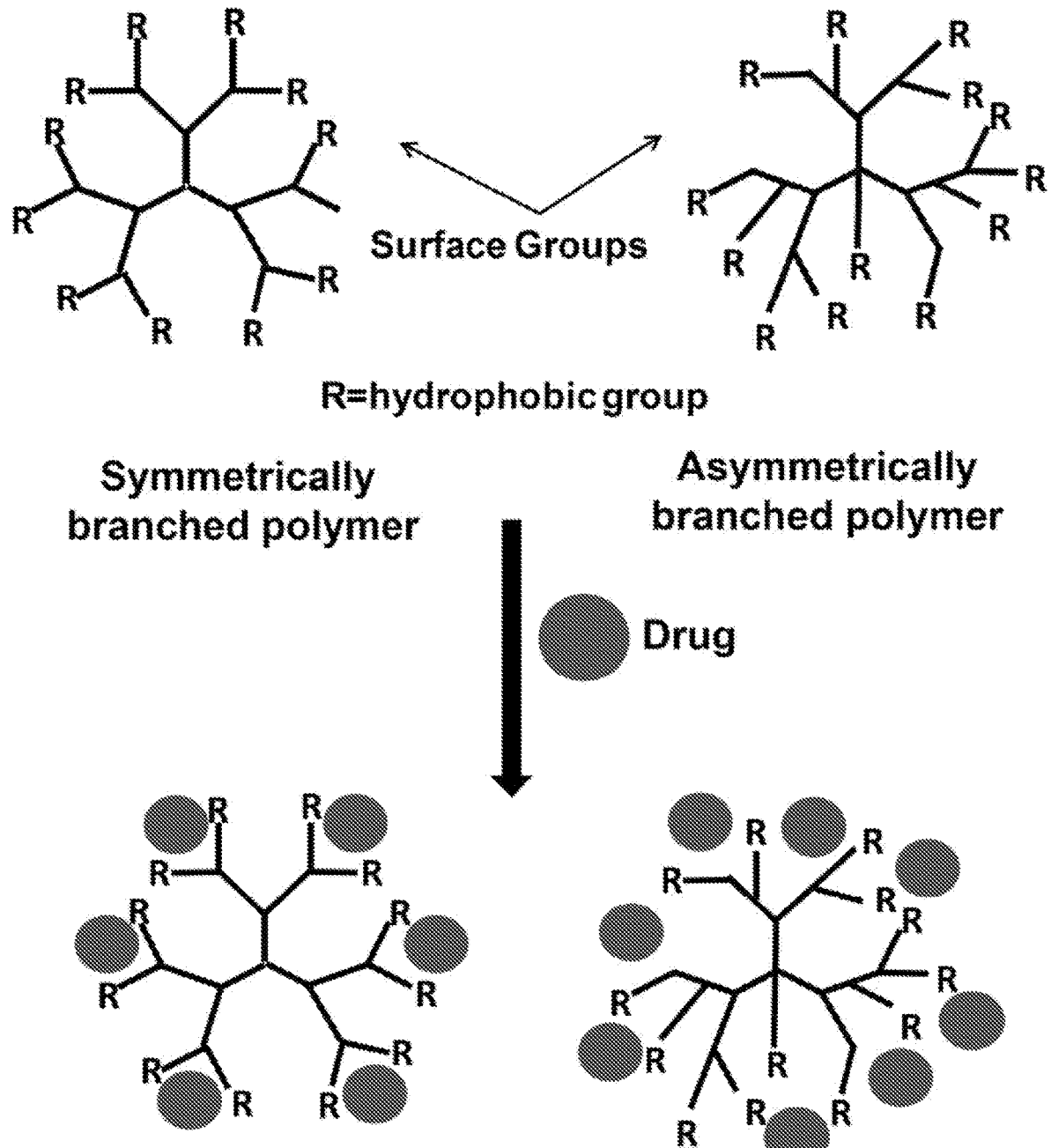
FIGS. 7A-B illustrate a drug loaded in or at the surface domain or region of the branched polymer SBP (FIG. 7A)

and ABP (FIG. 7B). In the and other figures, R indicates a surface group and a solid circle depicts a drug of interest.

Figure 8:
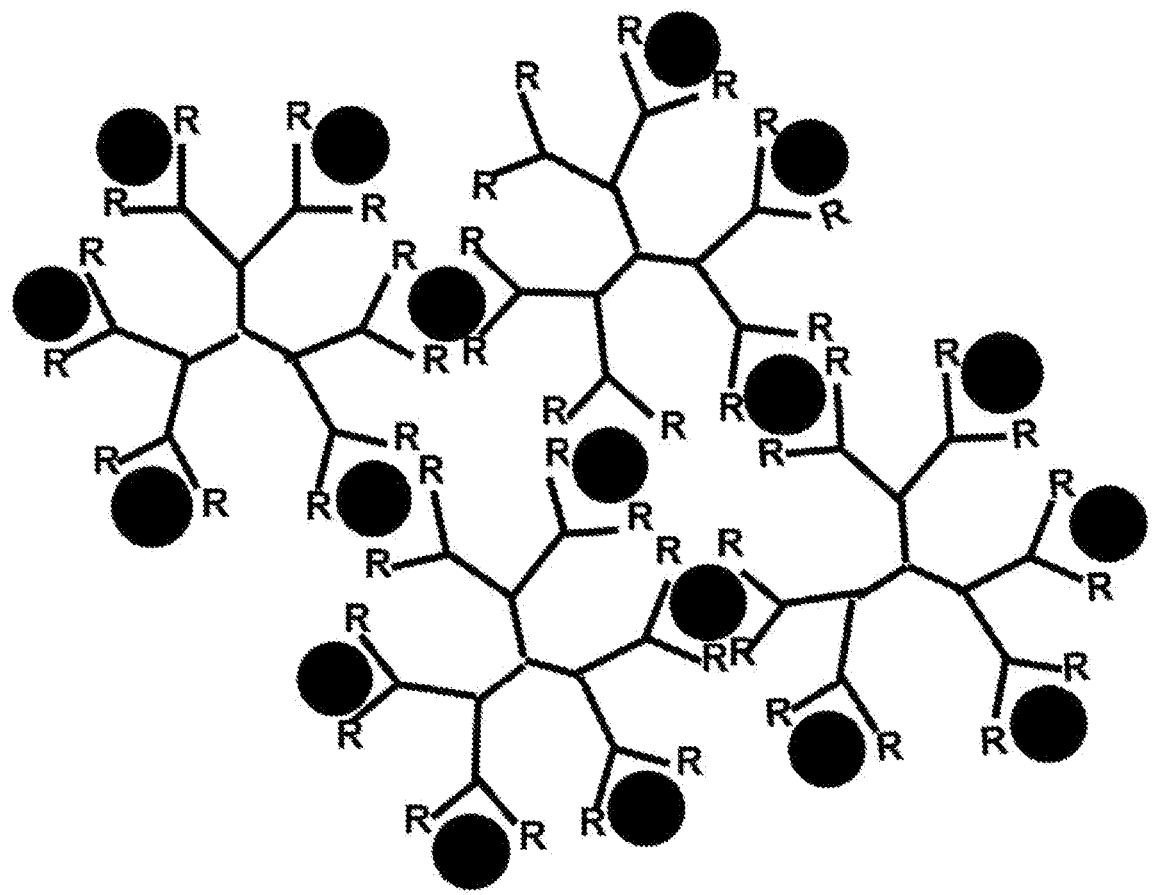

FIG. 8 illustrates one type of composite-based nanoparticles containing both drug molecules and branched polymers.

Figures 9A, 9B:
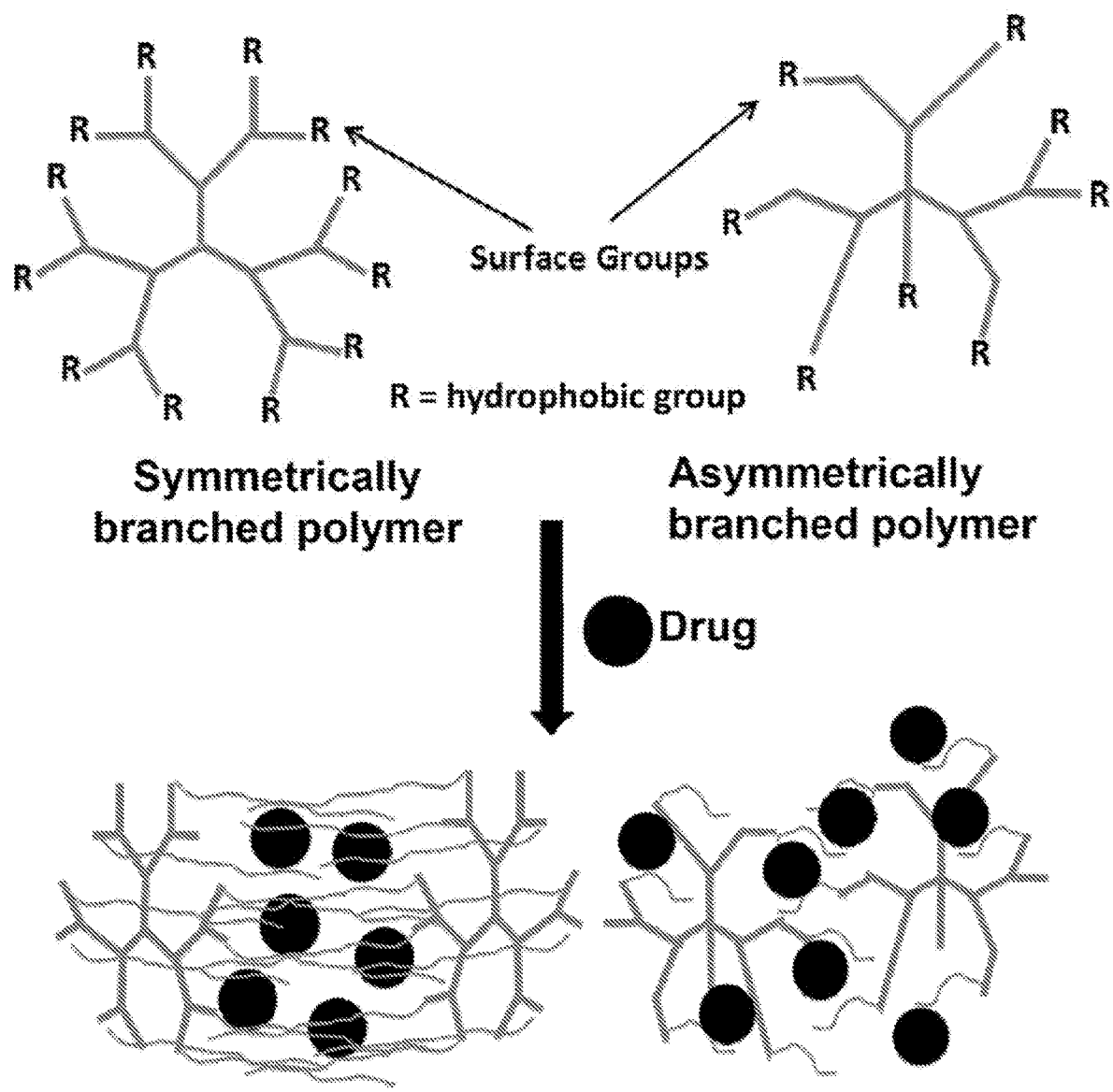

FIGS. 9A-B illustrate an insoluble or poorly water soluble drug that is loaded at hydrophobic surface groups of branched polymers SBP (FIG. 9A) and ABP (FIG. 9B). In the and other figures, a thin, wavy line depicts a hydrophobic surface group.

Figure 10A:
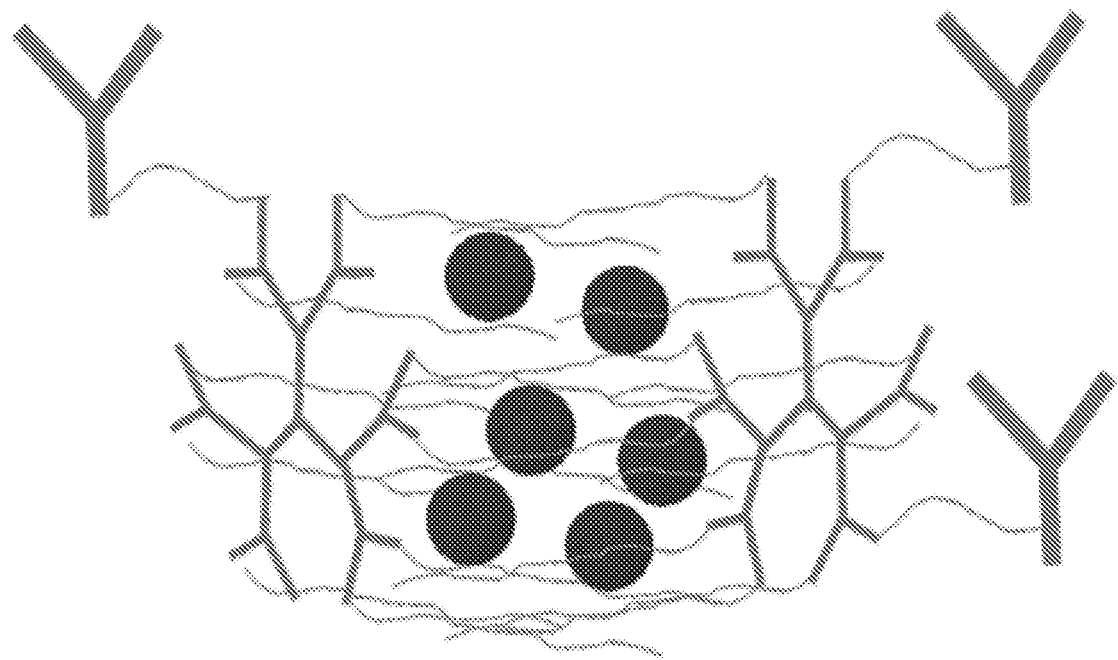
Figure 10B:
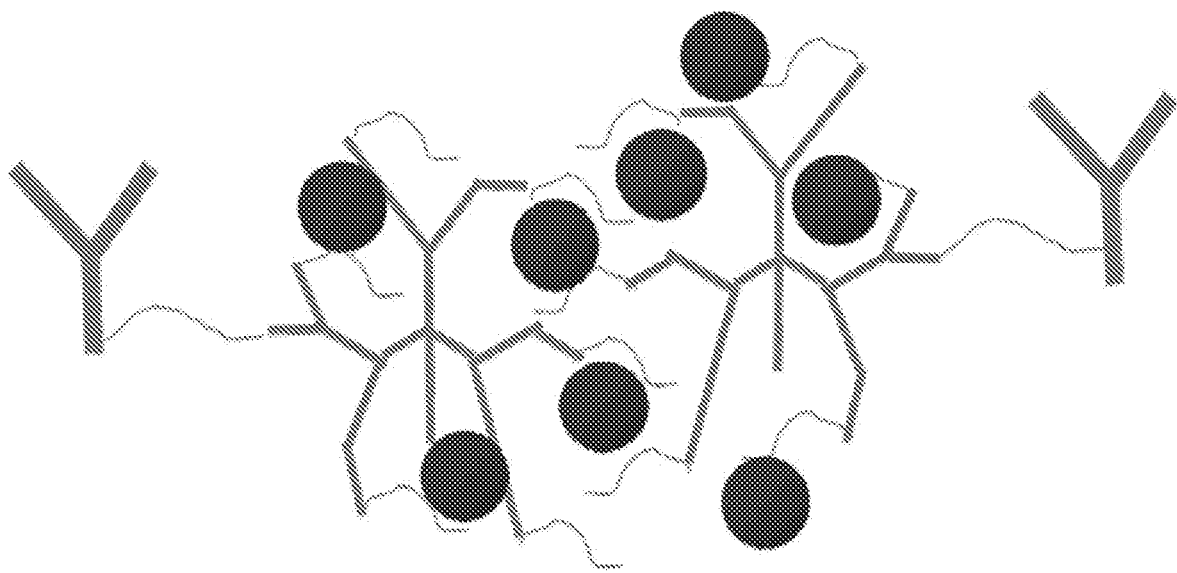

FIGS. 10A-B illustrate various drug-containing nanoparticles also carrying at least one targeting group or moiety, such as, an antibody, depicted herein and in other figures as a, "Y."

Figure 11:
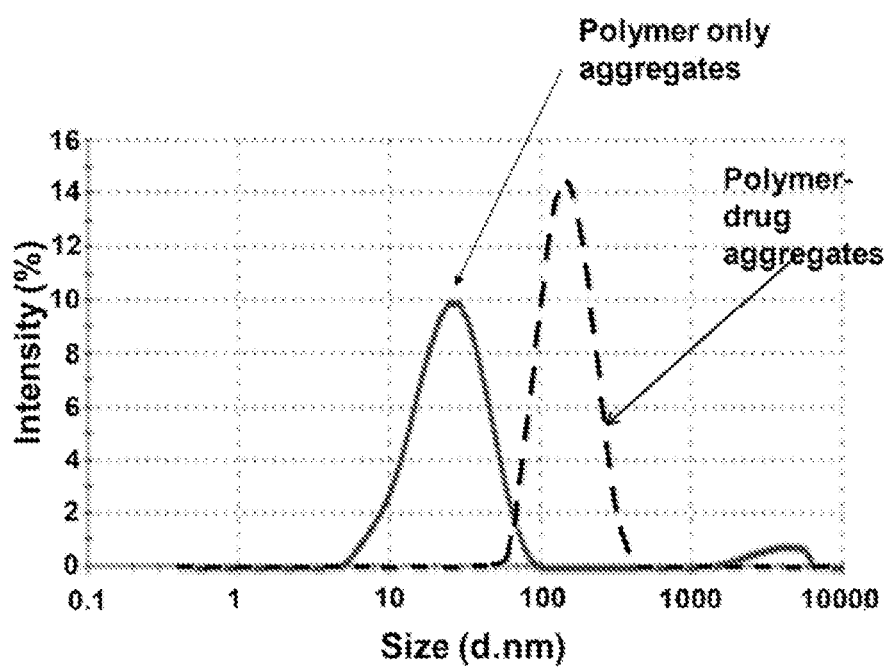

FIG. 11 shows the size comparison of polymer-only and polymer-drug aggregates with the polymer concentration at 25 mg/mL and the drug concentration at 5 mg/mL in saline. The polymer is a hydrophobically-modified, randomly-branched PEOX and the drug is paclitaxel.

Figure 12:
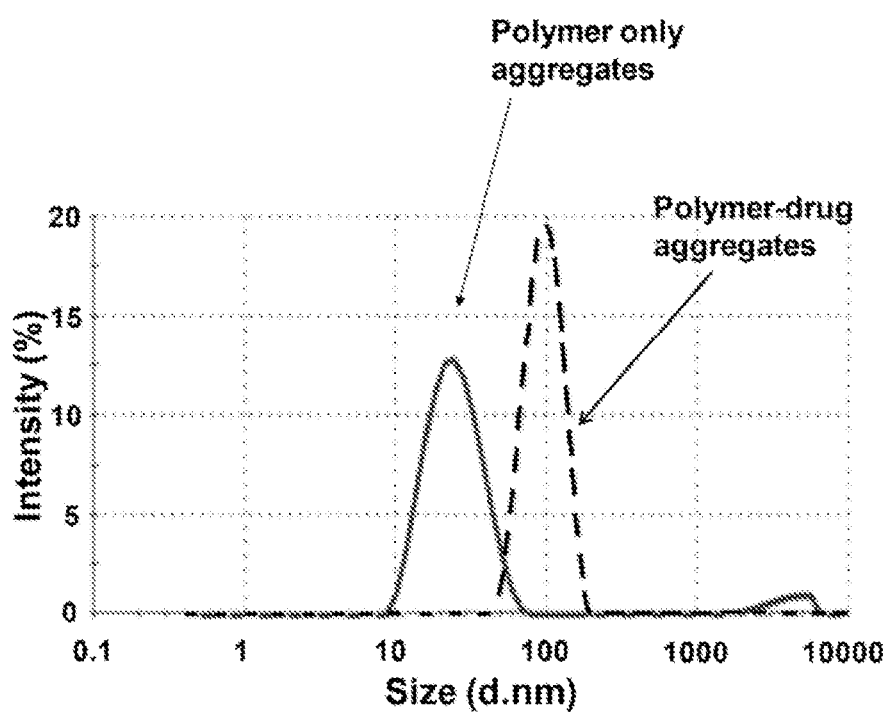

FIG. 12 shows the size comparison of polymer-only and polymer-drug aggregates with the polymer concentration at 2.5 mg/mL and the drug concentration at 0.5 mg/mL in saline. The polymer is a hydrophobically-modified, randomly-branched PEOX and the drug is paclitaxel.

Figure 13:
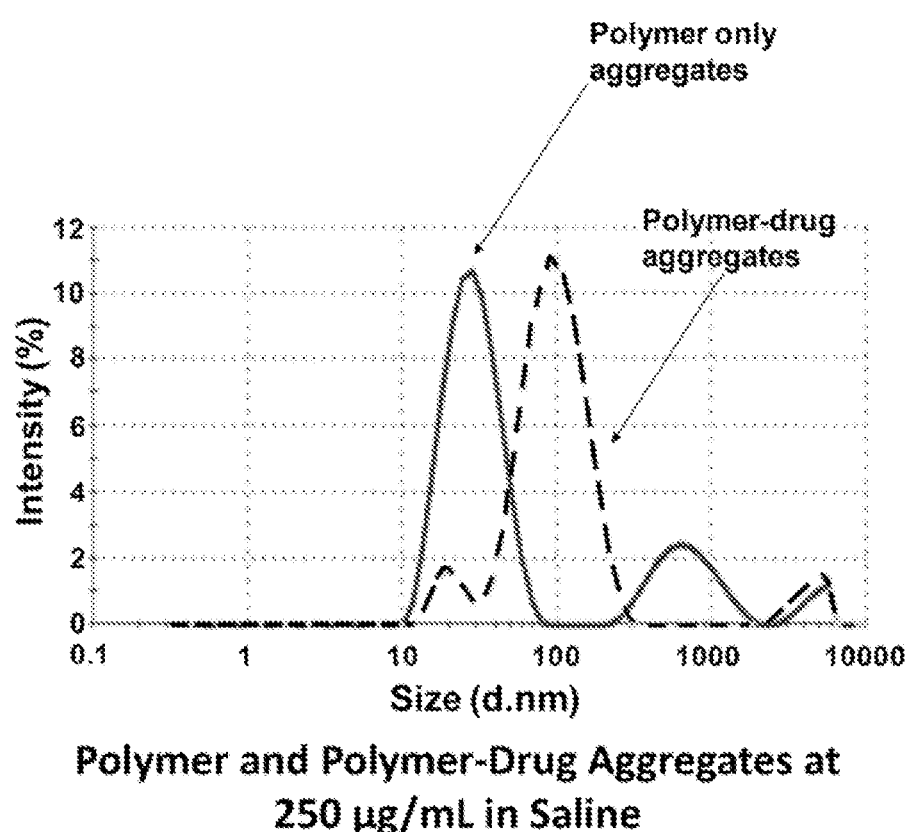

FIG. 13 shows the size comparison of polymer-only and polymer-drug aggregates with the polymer concentration at 250 µg/mL and the drug concentration at 50 µg/mL in saline. The polymer is a hydrophobically-modified, randomly-branched PEOX and the drug is paclitaxel.

Figure 14:
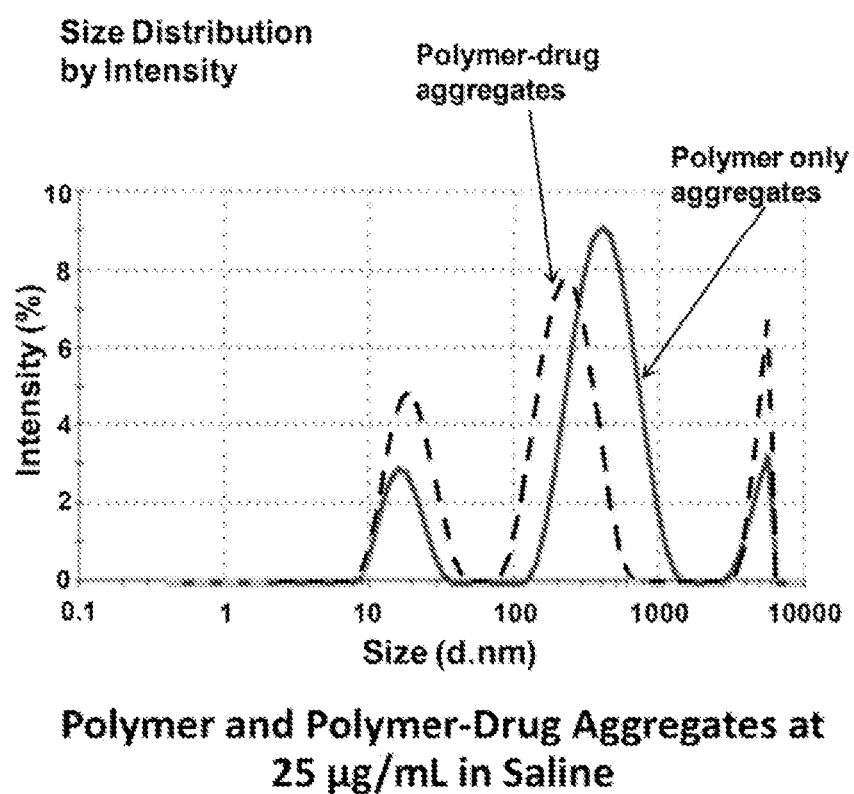

FIG. 14 shows the size comparison of polymer-only and polymer-drug aggregates with the polymer concentration at 25 µg/mL and the drug concentration at 5 µg/mL in saline. The polymer is a hydrophobically-modified, randomly-branched PEOX and the drug is paclitaxel.

Figure 15:
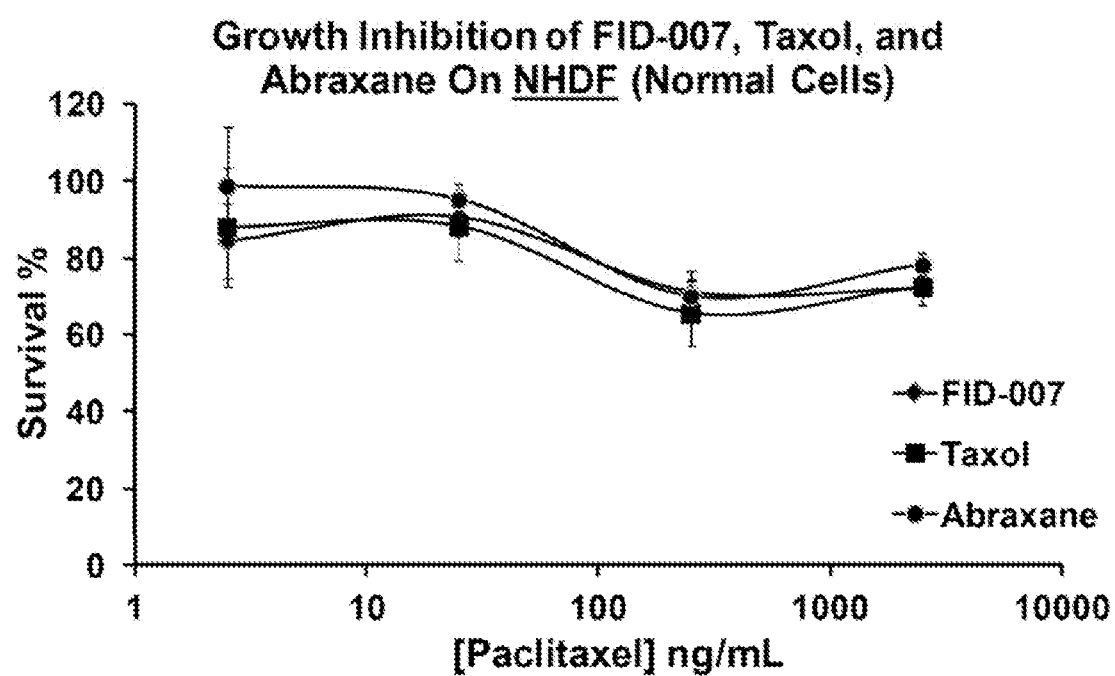

FIG. 15 depicts normal cell survival on exposure to three taxane formulations.

Figure 16:
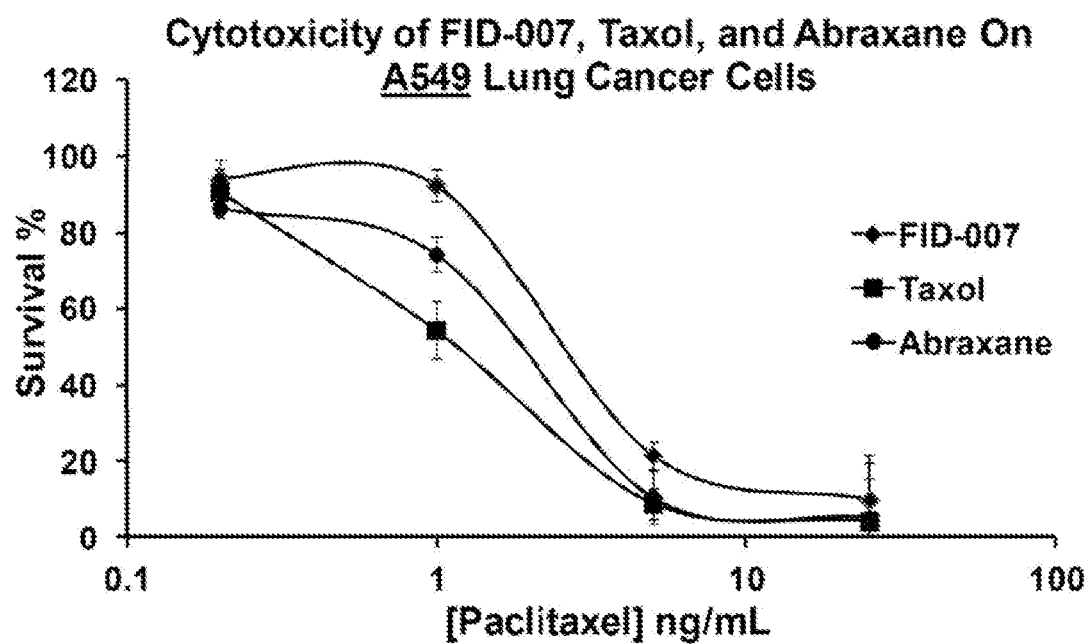

FIG. 16 depicts A549 lung cancer cell cytotoxicity on exposure to three different taxane formulations.

Figure 17:
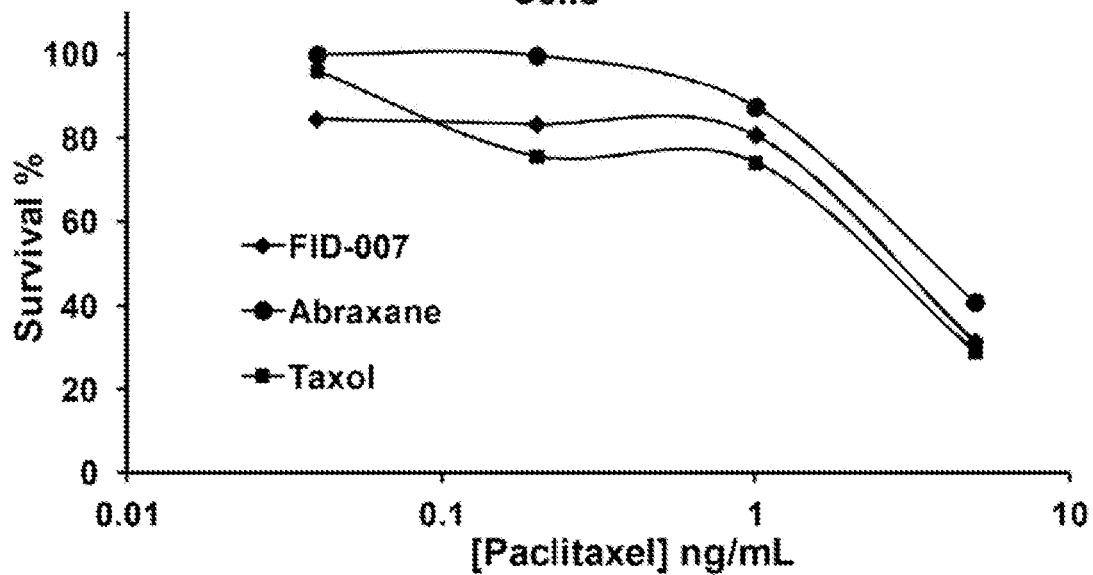

FIG. 17 depicts MDA-MB-231 triple negative breast cancer cytotoxicity on exposure to three different taxane formulations.

Figure 18:
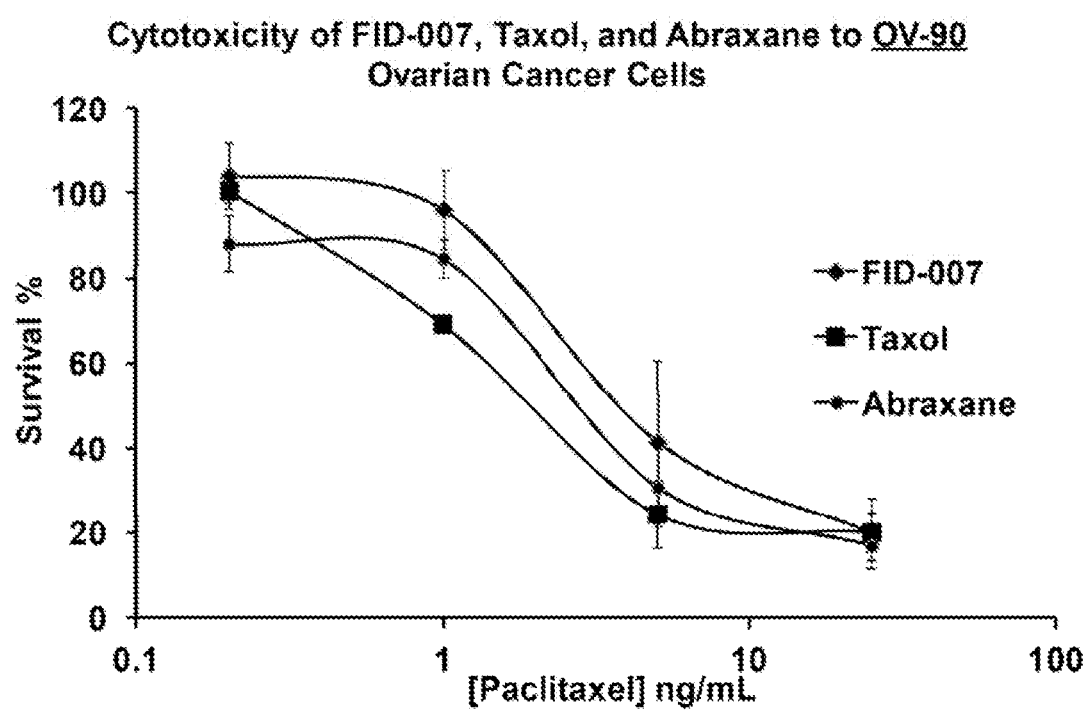

FIG. 18 depicts OV-90 ovarian cancer cytotoxicity on exposure to three different taxane formulations.

Figure 19:
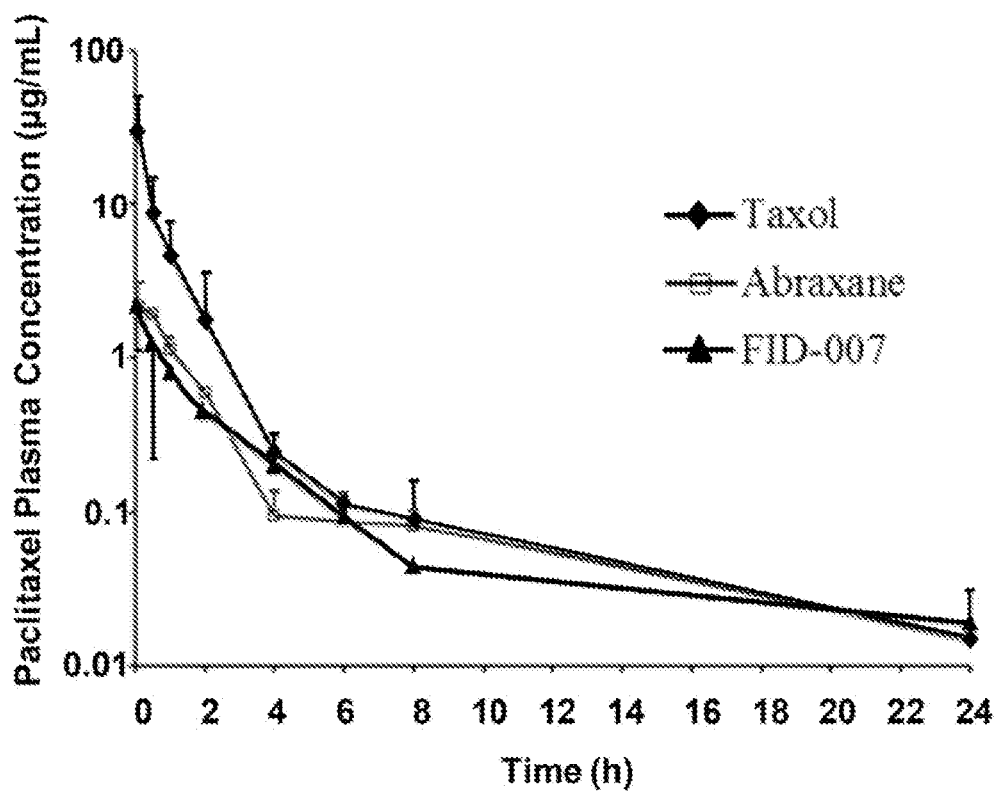

FIG. 19 depicts pharmacokinetic (PK) profiles of three different taxane formulations depicting plasma concentration over time.

Figure 20:
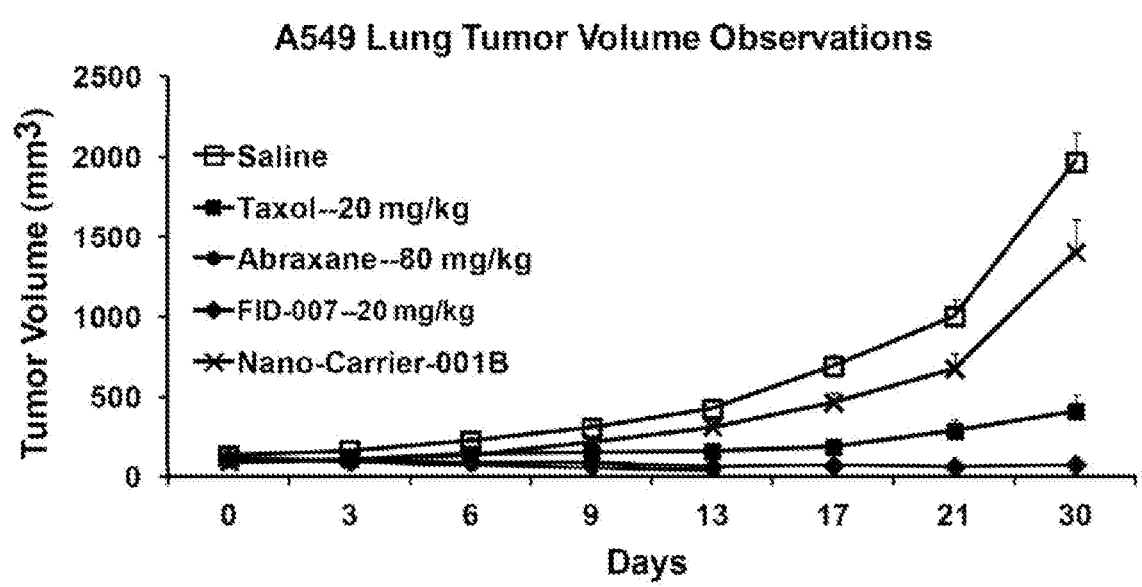

FIG. 20 depicts A549 lung cancer tumor volume in a mouse xenograft model with two control treatments and exposure to three different taxane formulations.

Figure 21:
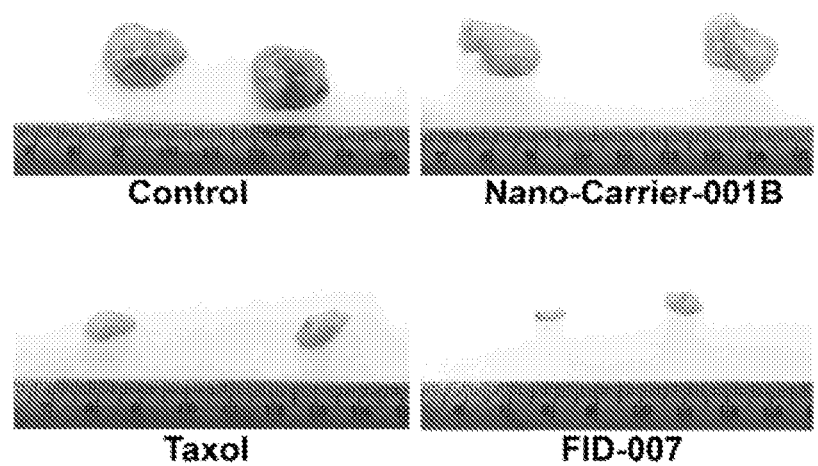

FIG. 21 presents images of excised lung cancer cell tumors grown as xenografts in a mouse and treatment of the mice with two controls and two forms of taxane.

Figure 22:
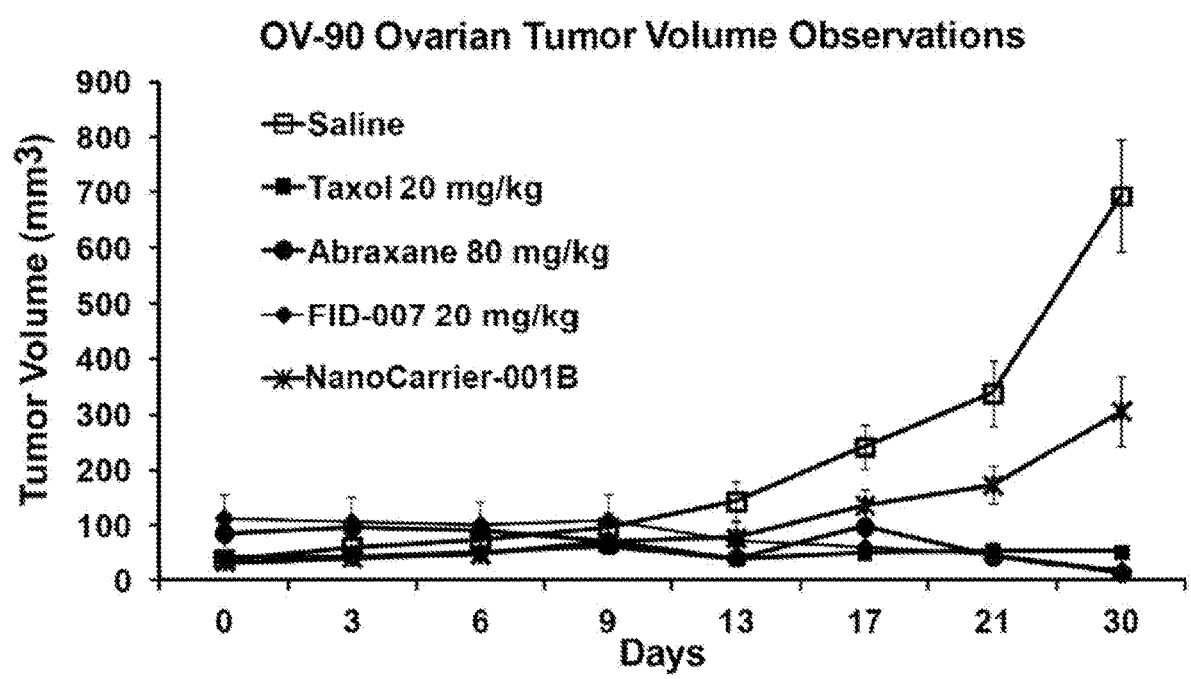

FIG. 22 depicts impact of two negative controls and three formulations of taxane on ovarian cancer tumor size in a mouse xenograft model.

Figure 23:
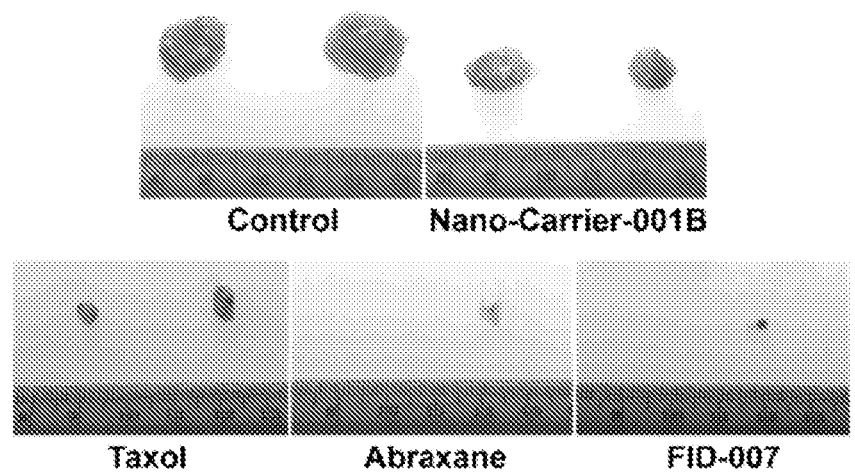

FIG. 23 presents images of excised ovary cancer cell tumors grown as xenografts in a mouse and treatment of the mice with two controls and three forms of taxane.

DETAILED DESCRIPTION

Features and advantages of the present invention will be more readily understood, by those of ordinary skill in the art, from reading the following detailed description. It is to be appreciated that certain features of the invention, which are described above and below in the context of separate embodiments, may also be provided in combination in a single embodiment. Conversely, various features of the invention that are, for brevity, described in the context of a single embodiment, may also be provided separately or in any combination or sub-combination. In addition, references in the singular may also include the plural (for example, "a" and "an" may refer to one, or one or more) unless the context specifically states otherwise.

Use of numerical values in the various ranges specified in this application, unless expressly indicated otherwise, are stated as approximations as though minimum and maximum values within the stated ranges were both proceeded by the word, "about". In this manner, slight variations above and below the stated ranges can be used to achieve substantially the same results as values within the ranges. Also, disclosure of ranges is intended as a continuous range including every value between the minimum and maximum values and including the minimum and maximum cited values.

The drug solubility in the instant disclosure is defined as, relative to parts of solvent required to solubilize one part of drug, <30 (soluble), 30-100 (poorly soluble) and >100 (insoluble). Taxane, such as paclitaxel and its derivatives, are water insoluble or poorly water soluble, when water is used as a solvent.

For the purposes of the instant disclosure, the words, such as, "about," "substantially," and the like are defined as a range of values no greater than 10% from the stated value or figure. "Homopolymer," is as described hereinabove.

Drug of Interest

The drug of interest described is a taxane and comprises paclitaxel and other taxane derivatives, such as, docetaxel. Paclitaxel is water-insoluble and has well-defined performance characteristics, such as, a low maximum tolerated dose (MTD), PK profile and limited efficacies in treating various types of cancer. The present disclosure covers the use of, for example, ABP's, as previously described, in improving those performance characteristics.

Nanocomposite, Nanoparticle or Nanoaggregate

A nanocomposite is a physical mixture of two or more materials or components (e.g., polymer and a taxane). In the instant disclosure, such a mixture could contain different nanoscopic phases or domains formed between a taxane and a branched homopolymer molecule in either solid or liquid state. Nanocomposites can include a combination of a bulk matrix (e.g., branched homopolymers and a taxane) and nanodimensional phase(s), which may exhibit different properties due to dissimilarities of structure and chemistry (e.g., the domain formed by a taxane and the surface groups of branched polymer, as well as the domains formed by the interior of the branched polymers). Since the solubility of the domains/phases may be different, on dissolving the nanocomposite in an aqueous solution, one of the phases may dissolve faster than the other or others, resulting in a gradual breakdown of the composite aggregate resulting in a graded and controlled release of the composite components and optionally, reformation of one or more of the components into a novel form, such as, a new aggregate. The terms, "nanocomposite," "nanoparticle" and "nanoaggregate," are equivalent and are used interchangeably herein.

The size of the aggregates described in the disclosure ranges from between about 10 to about 500 nm in diameter, from about 30 nm to about 300 nm in diameter. Aggregates may exhibit size-related properties that differ significantly from those observed for microparticles or bulk materials.

SBP's are depicted in FIG. 1A-1D, with symmetric branches, wherein all the homopolymers of interest possess a core and exhibit symmetric branch junctures consisting either of terminal or chain branches throughout the homopolymer. The functional groups are present predominantly at the exterior.

The modified SBP's can be obtained, for example, through chemically linking functional groups on, for example, symmetrically branched PAMAM or PPI dendrimers, commercially available from Aldrich, polyether dendrimers, polyester dendrimers, comb-branched/star-branched polymers, such as, those containing PEO, PEG, PMOX or PEOX, polystyrene, and comb-branched dendrigrafts, such as, those containing PEOX, PMOX or PEI.

Figure 1A:
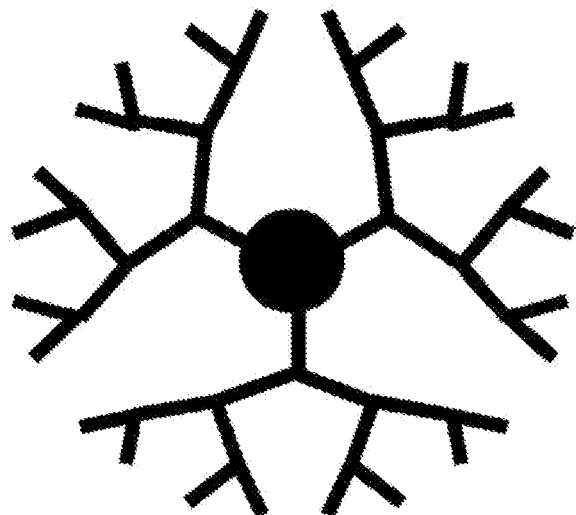
FIGS. 1A-D depict SBP's including a dendrimer (FIG. 1A), a dendrigraft (FIG. 1B), a comb-shaped polymer (FIG. 1C) and a star-shaped polymer (FIG. 1D). All have a core, whether globular or linear.
Figure 1B:
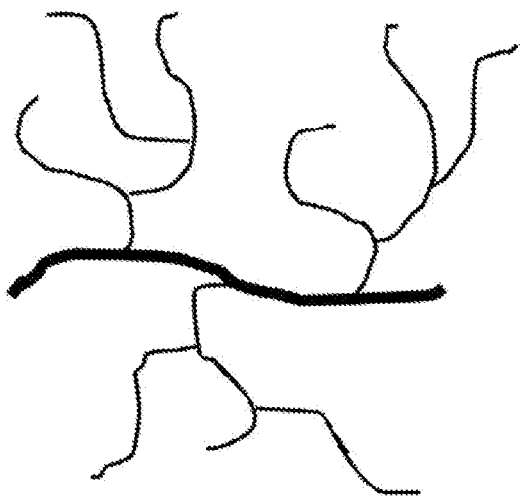
Figure 1C:
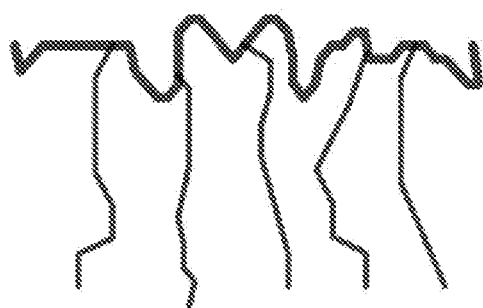
Figure 1D:
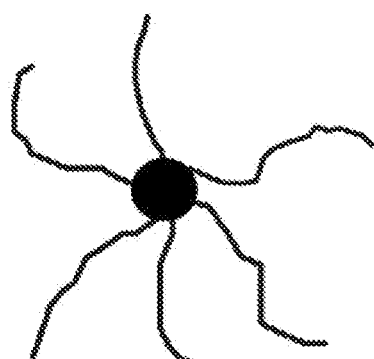
Figures 2A, 2B:
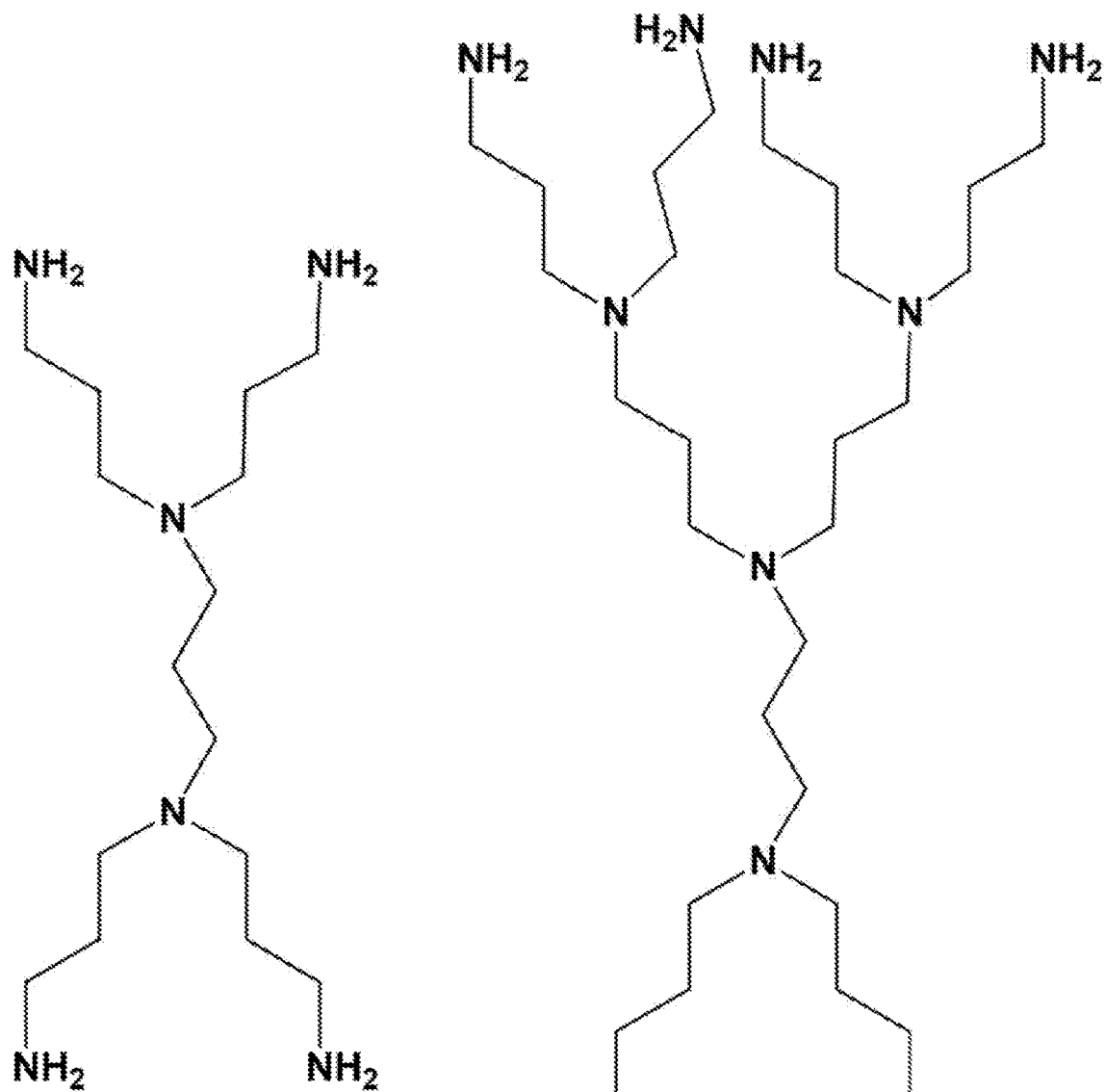
FIGS. 2A-B depict a chemical structure of symmetrically branched PPI dendrimers with 4 (FIG. 2A) and 8 (FIG. 2B) branches.
Figure 3:
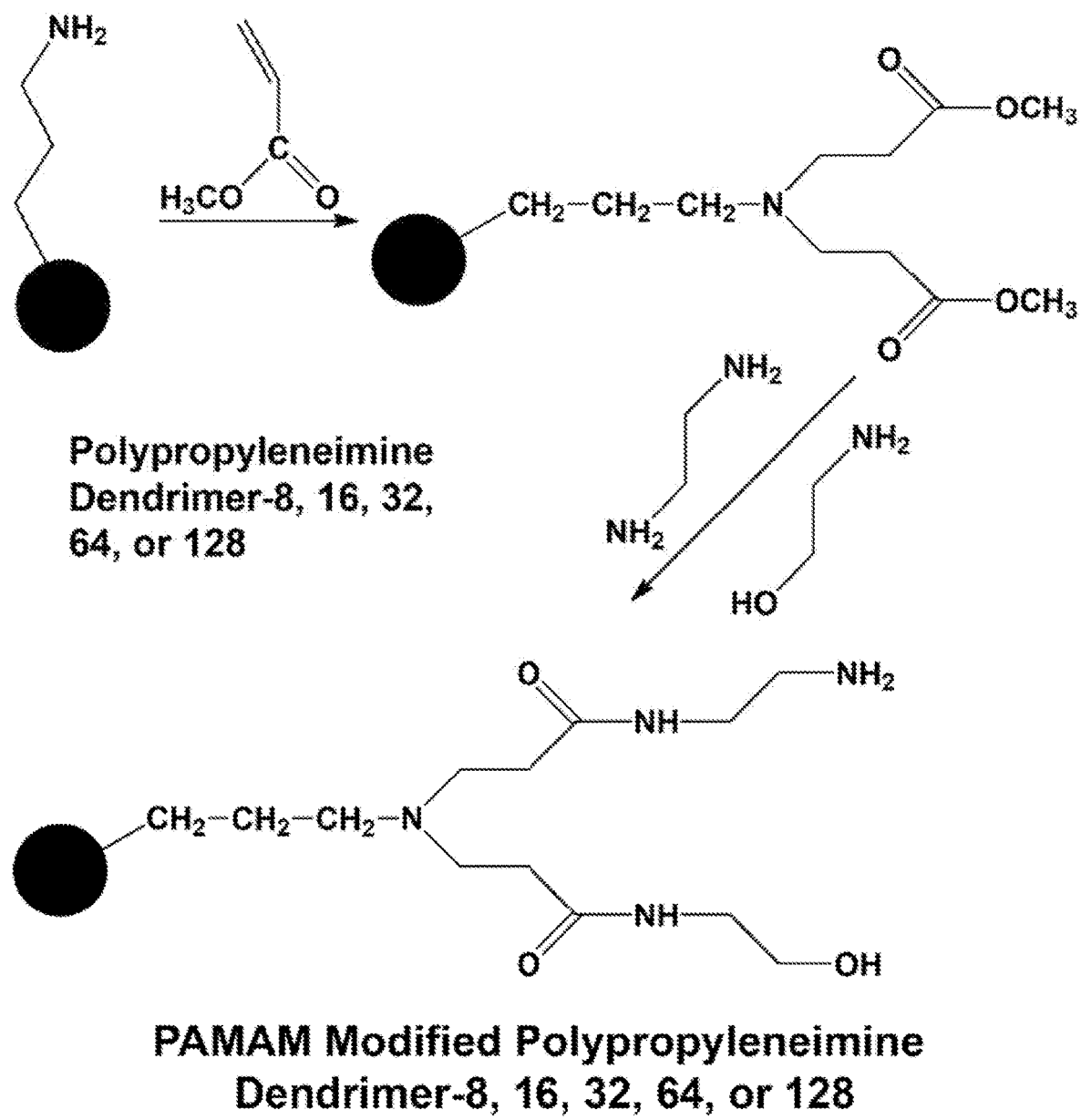
FIG. 3 depicts chemical modification reactions of symmetrically branched PPI dendrimers. The numbers, 8, 16, 32 and so on indicate the number of reactive groups at the surface of the dendrimer.

The synthetic procedures for making such SBP's/dendrimers are known (see, for example, "Dendrimers and Other Dendritic Polymers," Frechet & Tomalia, eds., John Wiley & Sons, Ltd., 2001) using commercially available reagents (for example, various generations of PPI dendrimers, such dendrimer-4 (FIG. 2A) and dendrimer-8 (FIG. 2B)) or a number of SBP's are commercially available. The synthesis of comb-branched and Combburst polymers is known (see, for example, U.S. Pat. Nos. 5,773,527; 5,631,329; and 5,919,442). Symmetrically branched PPI dendrimers can be chemically modified, for example via reactions illustrated in FIG. 3. The numbers, 8, 16, 32, 64 or 128 indicate the number of reactive groups at the surface of the dendrimer.

The higher branching densities of SBP's render the polymers molecularly compact with a well-defined interior void space, which makes such molecules suitable as a carrier for a taxane entrapped or encased, therein.

The surface modifications can enhance the properties and uses of the resulting modified SBP's. For example, with suitable modification, a water insoluble SBP can become water soluble, while an SBP with a high charge density can be modified to carry very low or no charge on the polymer or at the polymer surface. On the other hand, a water soluble SBP cm be modified with hydrophobic surface groups to enhance the ability to solubilize water insoluble or poorly water soluble drugs at the surface thereof. Modification can occur at any site of a polymer, for example, at a terminus, a branch, a backbone residue and so on.

In one embodiment of the instant disclosure, the SBP (for example, either a symmetrically branched PEI dendrimer, a PPI dendrimer, a PAMAM dendrimer or a symmetrically branched PEI dendrigraft, for example) can be modified with different kinds of, for example, primary amine groups through, for example, Michael addition or an addition of acrylic esters onto amine groups of the homopolymer. Thus, for example, through a Michael addition reaction, methyl acrylate can be introduced onto the primary and/or secondary amino groups of PEI, PPI and polylysine (PLL) homopolymers. The ester groups then can be derivatized further, for example, by an amidation reaction. Thus, for example, such an amidation reaction with, for example, ethylenediamine (EDA), can yield the addition of an amino group at the terminus of the newly formed branch. Other modifications to the homopolymer can be made using known chemistries, for example, as provided in, "Poly(amines) and Poly(ammonium salts)," in, "Handbook of Polymer Synthesis," (Part A), Kricheldorf ed., New York, Marcel Dekker, 1994; and, "Dendrimers and Other Dendritic Polymers" Frechet & Tomalia, eds., John Wiley & Sons, Ltd., 2001. Derivatives of EDA also can be used and include any molecular entity that comprises a reactive EDA, a substituted EDA or, for example, other members of the polyethylene amine family, such as, diethylenetriamine, triethylenetetramine, tetraethylenepentamine, pentaethylenehexamine, and so on including polyethylene amine, tetramethylethylenediamine and so on.

In embodiments, a modification can comprise a moiety that contributes to or enhances hydrophobicity of a polymer or a portion of a polymer. For example, hydrophobic functional groups, such as, aliphatic chains (e.g., hydrocarbon chains comprising 1 to about 22 carbons, whether saturated or unsaturated, linear, cyclic or branched), aromatic structures (e.g. containing one or more aromatic rings, which may be fused) or combinations thereof, can be used as a modifying agent and added to a polymer as taught herein practicing chemistries as provided herein.

On such addition, a modified SBP, such as, a modified PEI, PPI, PAMAM dendrimer or PEI dendrigraft, is formed. As an extension of the SBP, such as PPI and PEI, the resulting modified SBP also is symmetrically branched. Depending on the solvent environment (i.e. pH or polarity), the surface functional groups can carry different charge and/or charge density, and/or hydrophobic groups. The molecular shape and surface functional group locations (i.e., surface functional group back folding) then can be tuned further, based on those characteristic properties.

In another embodiment of the disclosure, the modified SBP's can be produced using any of a variety of synthetic schemes that, for example, are known to be amenable to reaction with a suitable site on the homopolymer. Moreover, any of a variety of reagents can be used in a synthetic scheme of choice to yield any of a variety of modifications or additions to the homopolymer backbone. Thus, for example, in the case of the Michael addition reaction to an amine described above, the addition of any of a variety of substituents can be used, for example, at the alkylation stage, using for example, any of a variety of acrylate reagents, such as, an acrylate comprising a hydrocarbon substituent, such as saturated or unsaturated hydrocarbons comprising 1 to about 22 carbons, which may be substituted, aliphatic, aromatic, ringed, saturated at one or more bonds or a combination thereof. Thus, suitable reactants include, methyl acrylate, ethyl acrylate, propyl acrylate, butyl acrylate, pentyl acrylate, hexyl acrylate, heptyl acrylate, octyl acrylate, nonyl acrylate, decyl acrylate, undecyl acrylate, dodecyl acrylate and so on, and mixtures thereof. Similarly, at the amidation stage in the example exemplified above, any of a variety of amines can be used. For example, EDA, monoethanolamine, tris(hydroxymethyl)aminomethane, alkyl amine, allyl amine or any amino-modified polymer, including those comprising PEG, PEO, perfluoropolymers, polystyrene, polyethylene, polydimethylsiloxane, polyacrylate, polymethylmethacrylate and the like, and mixtures thereof, can be used.

Such a synthetic strategy would allow not only symmetric growth of the molecule, where more branches with different chemical compositions can be introduced, but also the addition of multiple functional groups at the exterior of the structure. The precursor homopolymer can be modified, and continuously, using the same or a different synthetic process until the desired SBP's with appropriate molecular weight and functional groups are attained. In addition, the hydrophobic and hydrophilic properties, as well as charge densities of such polymers, can be tailored to fit specific application needs using appropriate monomers for constructing the homopolymer and suitable modification reactions.

In another embodiment of the disclosure, if a divergent synthetic procedure is used, the chain end of symmetrically star-branched or comb-branched homopolymer, such as, a poly(2-substituted oxazoline), including, for example, poly (2-methyloxazoline), poly(2-ethyloxazoline), poly(2-propyloxazoline) and poly(2-butyloxazoline, etc.), PEI, PEO/glycol, polyvinylpyrrolidone (PVP), polyphosphate, polyvinyl alcohol (PVA) or polystyrene, can be modified with another small molecule or polymer to generate various functional groups at the homopolymeric chain ends including a primary, secondary or tertiary amine, carboxylate, hydroxyl, aliphatic (e.g., hydrocarbon chain), aromatic, fluoroalkyl, aryl, PEG, PEO, acetate, amide and/or ester groups. Alternatively, various initiators also can be utilized so that the same type of functional groups can be introduced at the chain end if a convergent synthetic approach is utilized ("Dendritic Molecules," Newkome et al., eds., VCH, Weinheim, 1996; "Dendrimers and Other Dendritic Polymers," Frechet & Tomalia, eds., John Wiley & Sons, Ltd., 2001; and J. Macromol. Sci. Chem. A9(5), pp. 703-727 (1975)).

The initiator can be a hydrophobic electrophilic molecule, including hydrocarbons, aliphatic hydrocarbons, aromatic hydrocarbons or a combination of both, along with a halide functional group, such as, alkyl halides, aralkyl halides, acyl halides or combinations thereof. Examples of such compounds are monofunctional, initiators such as hydrocarbons containing from 1 to about 22 hydrocarbons with either saturated or unsaturated chemical bonds, such as, methyl iodide/bromide/chloride, ethyl iodide/bromide/chloride, 1-iodo/bromo/chloro butane, 1-iodo/bromo/chloro hexane, 1-iodo/bromo/chloro dodecane, 1-iodo/bromo/chloro octadodecane, benzyl iodide/bromide/chloride and so on. Other initiators include allyl bromides/chlorides. Acyl halides, such as, acyl bromide/chloride, benzoyl bromide/chloride and tosyl group-containing compounds, such as, p-toluenesulfonic acid, methyl tosylate and other tosylate esters can also be used. Any one or more initiators can be used in combination.

During polymerization, an initiator can be used to start polymerization. When used, various molar ratios of monomer to initiator can be used to obtain particular polymers. The particular polymers can have differing properties, such as, molecular size. Hence, suitable monomer to initiator molar ratios can be 20:1 to 80:1, such as, 25:1, 30:1, 35:1, 40:1, 45:1, 50:1, 55:1, 60:1, 65:1, 70:1 or 75:1 including 21:1, 22:1, 23:1, 24:1, 26:1, 27:1, 28:1, 29:1, 31:1, 32:1, 33:1, 34:1, 36:1, 37:1, 38:1, 39:1, 41:1, 42:1, 43:1, 44:1, 46:1, 47:1, 48:1, 49:1, 51:1, 52:1, 53:1, 54:1, 56:1, 57:1, 58:1, 59:1, 61:1, 62:1, 63:1, 64:1, 66:1, 67:1, 68:1, 69:1, 71:1, 72:1, 73:1, 74:1, 76:1, 77:1, 78:1, 79:1 and any other ratios within the range.

Figure 4A:
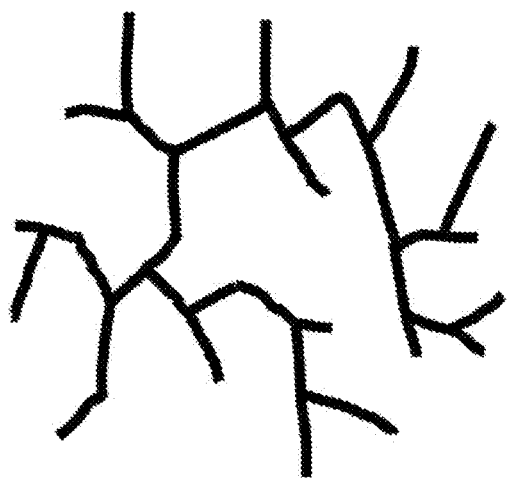
FIGS. 4A-B depict random (FIG. 4A) and regular (FIG. 4B) ABP's with asymmetric branch junctures and patterns.
Figure 4B:
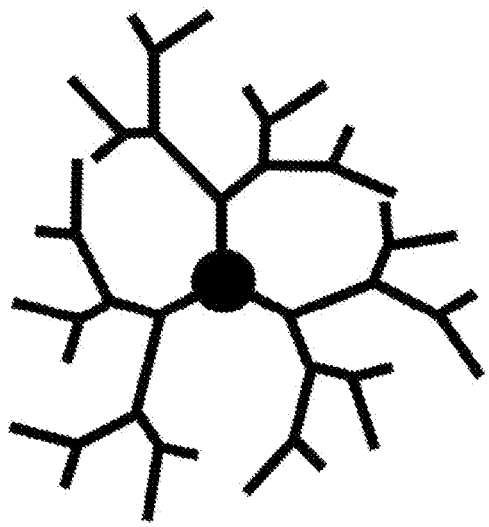

ABP's are depicted in FIG. 4A and FIG. 4B with asymmetric branches, wherein some of the polymers of interest possess no core and exhibit asymmetrical branch junctures consisting of both chain and terminal branches throughout the entire homopolymer. The junctional groups often are present both at the exterior and in the interior. However, when a larger functional group (e.g., a large hydrophobic or hydrophilic group) is used, the functional groups often can be attached preferentially and perhaps necessarily at the exterior of the ABP, for example, possibly due to steric effects. Therefore, such surface MBP's can be utilized for solubilization of or aggregate formation with an insoluble or poorly soluble drug.

The modified ABP's can be obtained, for example, through chemically linking functional groups on regular ABP's, such as, polylysine (e.g., branched PLL), on random ABP's, such as, PEI's (commercially available from Aldrich, Polysciences, or BASF under the trade name, LUPOSAL™) or polyoxazolines, which can be prepared according to the procedure of Litt (J. Macromol. Sci. Chem. A9(5), pp. 703-727 (1975)). Other ABP's can include, but are not limited to, polyacrylamides, polyphosphates, PVP's, PVA's etc.

A variety of known starting materials can be used. For making such modified ABP's. Such monomers and polymers are available commercially in large quantities at modest cost. For example, one such precursor monomer that can be used to synthesize a homopolymer of interest is PEI. The synthesis of random asymmetrically branched PEI's is known (Jones et al., J. Org. Chem. 9, 125 (1944)). PEI's with various molecular weights are available commercially from different sources, such as, Aldrich, Polyscienes and BASF (under the trade name LUPOSAL'). The random asymmetrically branched PEI's are produced primarily through cationic ring opening polymerization of ring-strained cyclic imine monomers, such as, aziridines (ethyleneimine) and azetidines (propyleneimine), with Lewis or Bronsted acids as initiators (Dernier et al., "Ethylenediamine and Other Aziridines," Academic Press, New York, (1969); and Pell, J. Chem. Soc. 71 (1959)). Since many of the methods are essentially one-pot processes, large quantities of random ABP's can be produced readily. Randomly branched poly (2-substituted oxazoline) polymers can be prepared using the procedure of Litt (J. Macromol. Sci. Chem. A9 (5), pp. 703-727 (1975)).

The synthetic processes for making ABP's often generate various branch junctures within the macromolecule. In other words, a mixture of terminal and chain branch junctures is distributed throughout the molecular structure. The branching densities of the random ABP's can be lower, and the molecular structure can be more open when compared with dendrimers and dendrigrafts. Although the branch pattern is random, the average ratio of primary, secondary and tertiary amine groups can be relatively consistent with a ratio of about 1:2:1, as described by Dick et al., J. Macromol. Sci. Chem., A4 (6), 1301-1314 (1970) and Lukovkin, Eur. Polym. J. 9, 559(1973).

The presence of the branch junctures can make the random ABP's, such as, asymmetrically branched PEI's, form, macromolecules with a possible spherical, ovoid or similar configuration. Within the globular structure, there are various sizes of pockets formed from the imperfect branch junctures at the interior of the macromolecule. Unlike dendrimers and dendrigrafts where interior pockets are always located around the center core of the molecule, the pockets of random ABP's are spread unevenly throughout the entire molecule. As a result, random ABP's possess both exterior and unevenly distributed interior functional groups that can be reacted further with a variety of molecules, thus forming new macromolecular architectures, a modified random ABP of interest.

Although having a core, the functional groups of the regular ABP are also distributed both at the exterior and in the interior, which is very similar to the random ABP. One such homopolymer is PLL, which can be made as described in U.S. Pat. Nos. 4,289,872; 4,360,646; and 4,410,688. Such homopolymers also can be modified in a manner similar as that for random ABP's, as taught herein, and as known in the art.

Figure 5:
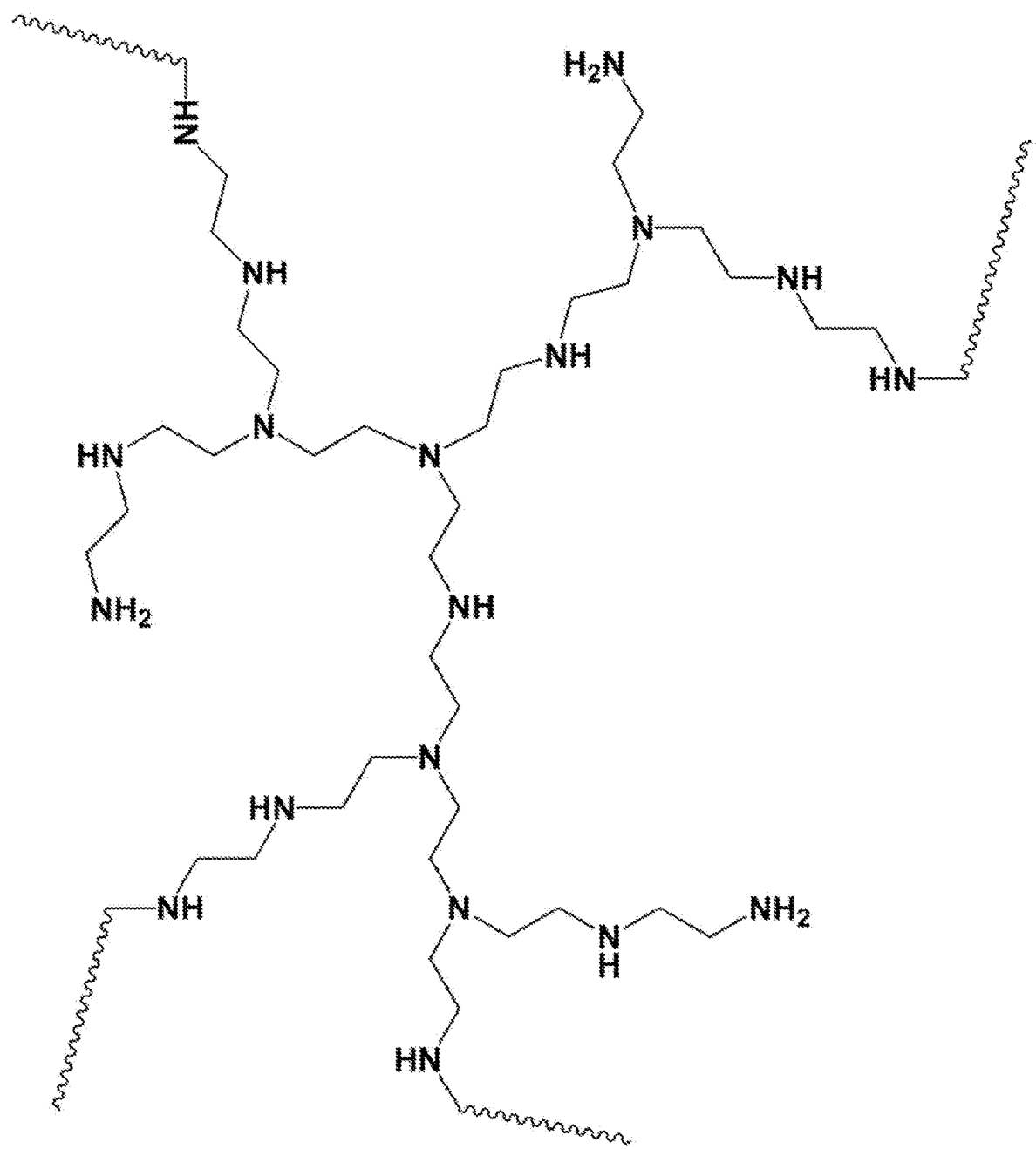
FIG. 5 depicts a chemical structure of a random asymmetrically branched PEI homopolymer.

In an embodiment of the disclosure, the ABP (for example, either a random asymmetrically branched PEI or a regular asymmetrically branched PLL) is modified with different kinds of primary amine groups through, for example, Michael addition or an addition of acrylic esters onto amines of the polymer. Thus, for example, through a Michael addition reaction, methyl acrylate or other acrylates as provided herein can be introduced onto the primary and/or secondary amino groups of, for example, PEI and PLL homopolymers. The ester groups then can be further derivatized, for example, by an amidation reaction. Thus, for example, such an amidation reaction with, for example, EDA, can yield the addition of an amino group at the terminus of the newly formed branch. Other modifications to the polymer can be made using known chemistries, for example, as provided in "Poly(amines) and Poly(ammonium salts)" in "Handbook of Polymer Synthesis" (Part A), Kricheldorf, ed., New York, Marcel Dekker, 1994. An example of a random asymmetrically branched PEI homopolymer is shown in FIG. 5.

On such addition, a modified ABP, such as, a modified PEI or PLL homopolymer, is formed. As an extension of the ABP, such as PEI and PLL, the resulting modified ABP also is branched, asymmetrically. Depending on the solvent environment (i.e. pH or polarity), the surface functional groups can carry different charge and charge density. The molecular shape and functional group locations (i.e., functional group back folding) then cars be further tuned, based on those characteristic properties.

In another embodiment, the modified ABP's can be produced using any of a variety of synthetic schemes that, for example, are known to be amenable to reaction with a suitable site on the homopolymer. Moreover, any of a variety of reagents can be used in a synthetic scheme of choice to yield any of a variety of modifications or additions to the polymer backbone. Thus, for example, in the case of the Michael addition reaction to an amine described above, the addition of any of a variety of substituents can be used at the alkylation stage, as provided hereinabove, for example, with an acrylate, which can comprise a saturated or unsaturated hydrocarbon, such as one comprising one carbon to about 22 carbons, which may be aliphatic, branched, saturated, aromatic, ringed or combination thereof. Suitable reactants include methyl acrylate, ethyl acrylate, propyl, acrylate, butyl acrylate, pentyl acrylate, hexyl acrylate, heptyl acrylate, octyl acrylate, nonyl acrylate, decyl acrylate, undecyl acrylate, dodecyl acrylate and the like, and mixtures thereof. Similarly, at the amidation stage in the example exemplified above, any of a variety of amines can be used in the methods provided herein and known in the art. For example, EDA, monoethanolamine, tris(hydroxymethyl)aminomethane, alkyl amine, allyl amine or any amino-modified polymers, including PEG, perfluoropolymers, polystyrene, polyethylene, polydimethylsilixane, polyacrylate, polymethylmethacrylate and the like, and mixtures thereof, can be used. In addition, the linking of the hydrophobic groups, including aliphatic (e.g., hydrocarbons from $C_1$ to about $C_{22}$) groups, aromatic groups, polyethylene polymers, polystyrene polymers, perfluoropolymers, polydimethylsiloxanes, polyacrylates, polymethylmethacrylates, as well as, hydrophilic groups, including a OH group, hydrophilic polymers, such as, PEOX, PEG, PEO etc. to a modified ABP can be achieved by using, for example, epoxy reactions, amidation reactions, Michael addition reactions, including using an —SH or an —NH$_2$ group reacted with maleimide, aldehyde/ketone-amine/hydrazide coupling reactions, iodo/iodoacetyl-SH coupling reactions, hydroxylamine-aldehyde/ketone coupling reactions etc. Such synthetic strategies allow not only asymmetric growth of the molecule, where more pockets are introduced, but also the addition of multiple functional groups at both the interior and the exterior of the structure. The homopolymer can be modified further using the same or a different synthetic process until the desired ABP's with appropriate molecular weight and functional groups are attained. In addition, the hydrophobic and hydrophilic properties, as well as charge density of such homopolymers, can be tailored to fit specific application needs using appropriate monomers for constructing the homopolymer and suitable modification reactions.

In another embodiment of the disclosure, a focal point (merged from various reactive chain ends during a convergent synthesis) of a random ABP, such as, PDX, can be terminated or reacted with another small molecule to generate various functional groups at the homopolymeric chain ends, including primary, secondary or tertiary amines, carboxylate, hydroxyl, alkyl, fluoroalkyl, aryl, PEG, acetate, amide and/or ester groups. Alternatively, various initiators also can be utilized so that the same type of functional group can be introduced at the surface groups where a polymerization begins during a convergent synthesis (J. Macromol. Sci. Chem. A9 (5), pp. 703-727(1975)).

Figure 6A:
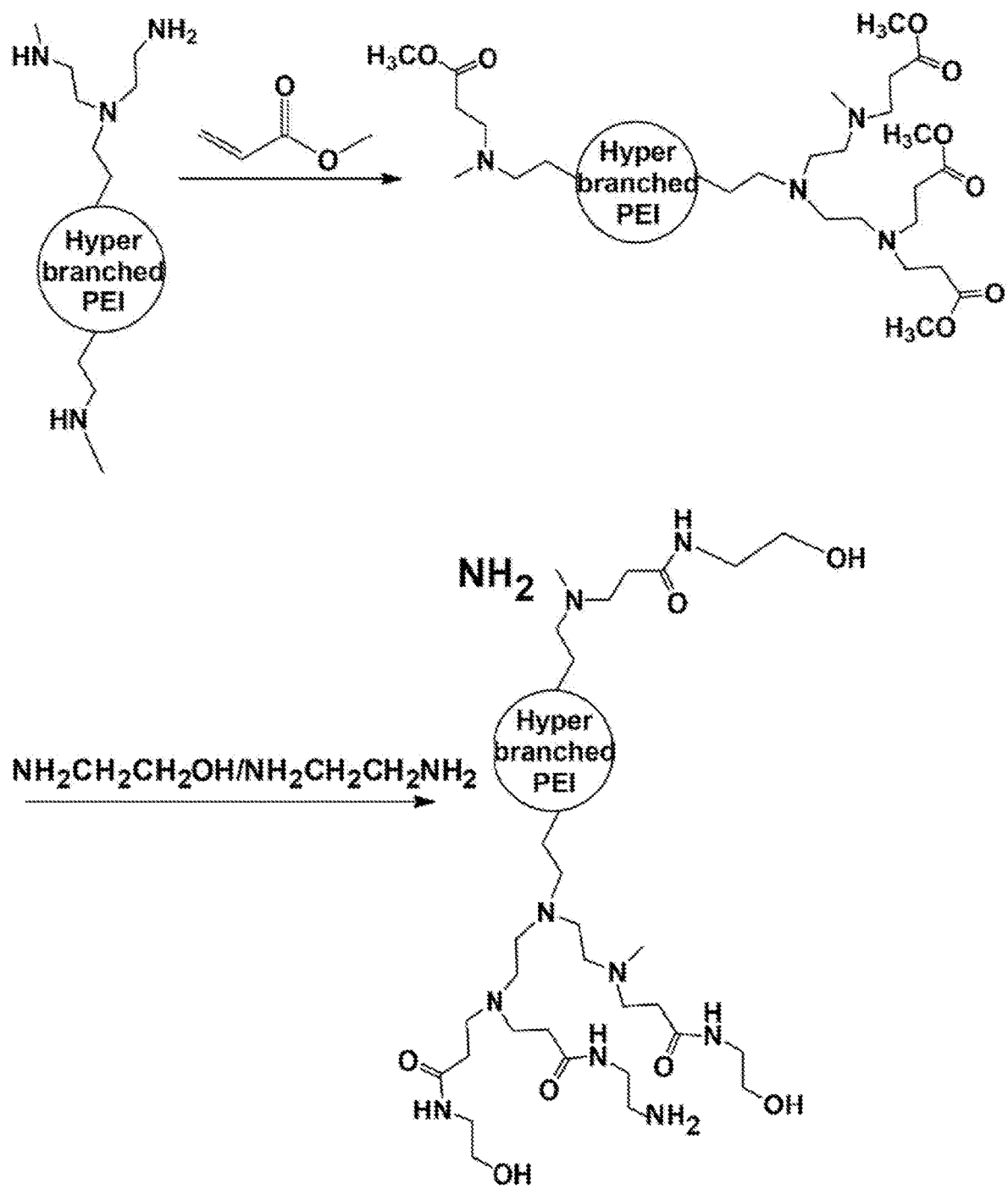
FIGS. 6A-B depict synthetic schemes.
Figure 6B:
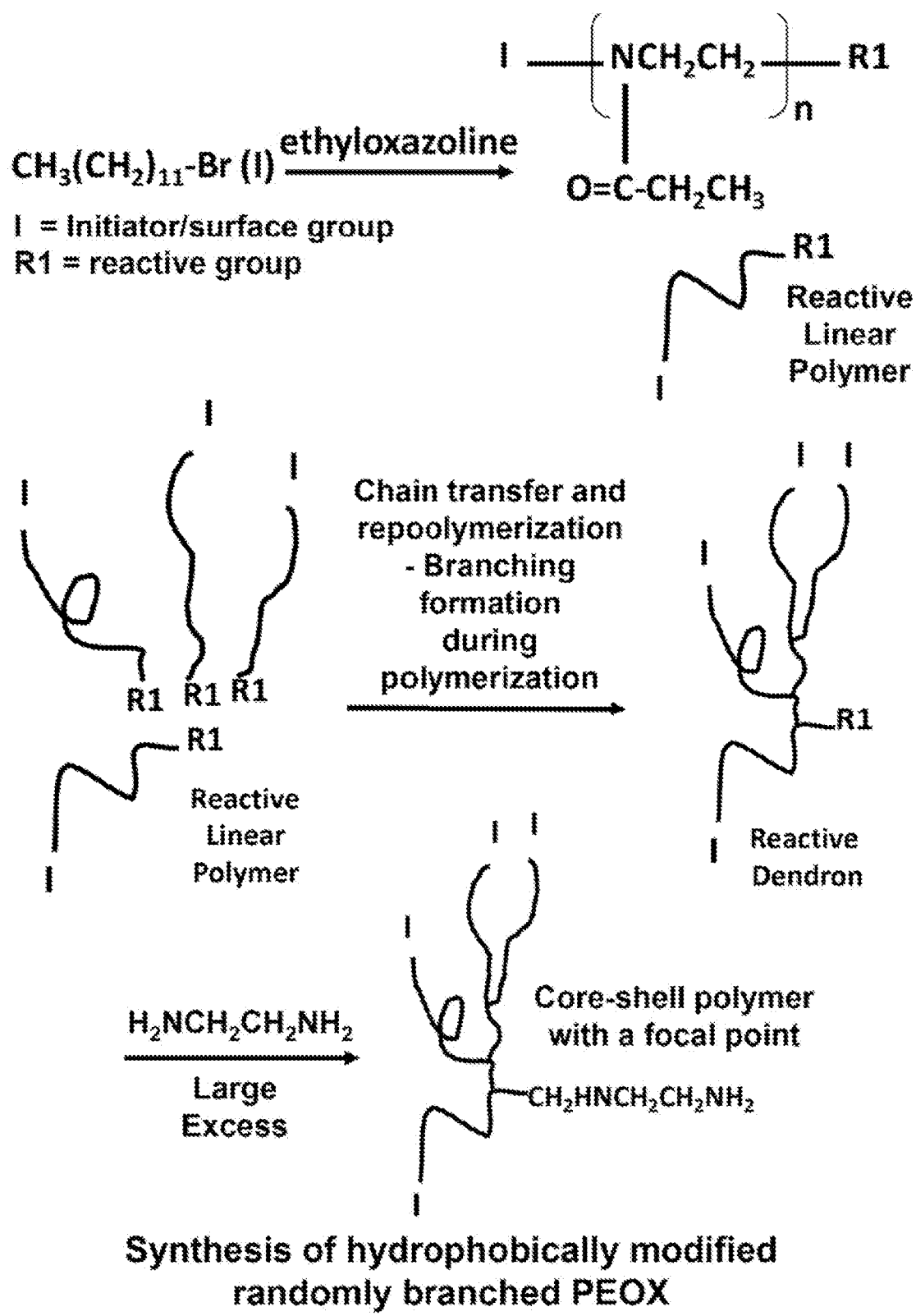

An alkyl surface-modified, randomly branched poly(2-ethyloxazoline) with a primary amine group at the focal point of the branched polymer can be prepared using the Litt and Warakomski procedures, supra. For example, $CH_3(CH_2)_{17}$—Br can be utilized as an initiator for 2-ethyloxazoline polymerization through a cationic ring opening process to generate a randomly branched polymer, followed by quenching with N-ten-butyloxycarbonylpiperazine (N-Boc-piperazine) or EDA. The termination with a large excess of EDA allows the hydrophobically modified branched poly(2-ethyloxazoline) polymer to be functionalized with a primary amine group at the focal point (FIG. 6B). Alternatively, N-Boc-piperazine-terminated hydrophobically-modified branched poly(2-ethyloxazoline) polymer also can be deprotected to generate a free amino group at the focal point. If not terminated, the focal point of the polymer can be hydrolyzed to, for example, a hydroxyl group on dissolving in water (e.g., containing, for example, 1N $Na_2CO_3$).

While the introduction of a primary amine group to a hydrophobically-modified branched poly(2-oxazoline) homopolymer enhances drug solubility and produces taxane-induced aggregates, the primary amine group also allows the attachment of various targeting groups, such as, an antibody, antigen-binding portion thereof an antigen or a member of a binding pair, such as, to the hydrophobically modified branched poly(2-oxazoline) polymer (FIG. 10). Such aggregates or nanoparticles containing such targeting groups and modifications thereto can provide a targeting ability on the aggregate with a taxane and enable taxane to be released preferentially or solely at the desired treatment location.

As taught herein, the MBP's, such as, a hydrophobically-modified homopolymers, including both SBP's and ABP's, can be used to generate an encapsulating polymer or nanocapsule for solubilizing water insoluble or poorly water soluble taxanes, or for forming taxane-induced nanoparticles with water insoluble or poorly water soluble taxanes, such as, paclitaxel (FIG. 7A-7B, FIG. 8 and FIG. 9). In an organic solvent environment, the hydrophilic or amphiphilic interior can be poly(2-oxazoline), poly(2-substituted oxazolines), including poly(2-methyloxazoline, poly(2-ethyloxazoline), poly(2-propyloxazoline) and poly(2-butyloxazoline) etc., PEG, PEO, polyphosphonate and the like. The hydrophobic exterior can comprise aliphatic hydrocarbons (such as, from $C_1$ to about $C_{22}$), aromatic hydrocarbons, polyethylene polymers, polystyrene polymers, perfluoropolymers, polydimethylsiloxanes, polyacrylates, polymethylmethacrylates and the like. In an aqueous environment, the reverse is true. In the drug-induced aggregates in an aqueous environment, the drug molecules such as taxanes are associated with the hydrophobic groups/domains of the MBP's (FIG. 9). The branching density (e.g., from low generation, such as, star and comb homopolymers, to high generation of dendrimers and dendrigrafts), as well as the amount of hydrophobic surface group coverage (e.g., from 0% to 100% coverage) of the branched homopolymers can affect significantly homopolymer solubility, which in turn, also affects the ability to dissolve or to adsorb/absorb a taxane. For example, the increase in branching density and the amount of hydrophobic group coverage will make the homopolymer more compatible with a taxane.

In some cases, the ABP's and SBP's with from about 0.1 to about 30% or more surface hydrophobic component by weight are effective at solubilizing or dispersing poorly water soluble or water insoluble taxanes, such as, paclitaxel. In addition, the branched homopolymers utilized, for example, a PDX, a PEOX, a PMOX, PEO/PEG, polyacrylamides, polyphosphates, PVP's and PVA's are soluble in both water and in various organic solvents, thereby facilitating forming various taxane-containing nanoparticles or aggregates. The good water solubility along with good hydrophobic drug miscibility in an aqueous solution, with or without other organic solvents, makes such homopolymers useful for enhancing the solubility of poorly water soluble taxanes. For example, the homopolymers of interest simplify manufacturing processes and decrease production cost by reducing formulation steps, processing time, as well as the need to use complex and expensive equipment currently used in the pharmaceutical industry. If additional branching densities are needed, the SBP's or ABP's first can be modified with additional groups as described herein, and then, for example, attached with additional hydrophobic functional groups for enhancing taxane solubility.

On mixing hydrophobically-modified SBP's or ABP's with a water insoluble or poorly water soluble taxane, such as, paclitaxel, a distinct physical aggregate is formed of size distinct from aggregates formed only of polymer (FIG. 11-FIG. 14). When the homopolymer and taxane concentrations decrease, the size and distribution of the polymer/taxane aggregates become much more similar to that of polymer only aggregates suggesting taxane is released from the induced aggregates or nanoparticles. The broad size distribution of polymer-only aggregates is similar to that observed for other structures composed of lipid, whether or not associated with a taxane. On the other hand, the taxane-induced aggregates of interest are of a particular size of narrower distribution, that is, unique aggregates of certain size are produced. As taxane concentration in the aggregate decreases, homopolymer concentration in the aggregate decreases, aggregate concentration decreases or any combination thereof, the aggregates of interest release paclitaxel, as evidenced by a reduction of aggregate size and/or a broader distribution of aggregate size. The broader distribution may result from a mixture of homopolymer-only aggregates and polymer/taxane aggregates of varying size due to taxane release, until the only aggregates observed are those which have the characteristics of those which are homopolymer only. In other words, taxane is released gradually after introduced into a host, such as, in the circulatory system. That mechanism is important for various drug delivery applications including, intravenous (IV), oral, transdermal, ocular, intramuscular and the like modes of administration, and where a delayed release or sustained release profile may be desirable.

For simplicity, the term "polymer" used in describing aggregate, polymer-drug nanoparticles, polymer aggregate, or polymer to drug ratio, etc., include SBP and ABP disclosed in this application, and include modified polyoxazoline, such as, hydrocarbon modified polyoxazolines including those further modified with EDA or EDA derivative disclosed herein.

Suitable weight ratios of polymer to taxane are 6:1 to 8:1, such as, 6.5:1, 7:1 or 7.5:1, including each and all of 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, and all ratios within the range.

Applicants unexpectedly discovered that the combination of the molar ratio of monomer to initiator in the polymerization and the weight ratio of polymer to taxane in the nanoparticles can affect large scale manufacturability of the drug nanoparticles, nanoparticle size, and efficacy as a tumor-reducing treatment. As an example, taxane-induced aggregates prepared with a polymer:taxane weight ratio of 5:1, using a polymer synthesized with 100:1 monomer:initiator molar ratio results in larger nanoparticles, for example, in the 120-140 nm range before lyophilization. Such large nanoparticles are difficult to pass through a 0.22 μm filter (a required sterilization step for injectables) when manufactured in large quantities.

In comparison, when a polymer synthesized using a monomer:initiator molar ratio of 60:1 is mixed with taxane with, a polymer:taxane weight ratio of 7:1, the nanoparticles formed can be 70-100 nm in size before lyophilization, which allows the particles to pass through a 0.22 μm filter with little difficulty.

Smaller nanoparticles at about 100 nm or less in size before lyophilization reduced tumors at lower dose concentrations than did larger particles. For example, smaller nanoparticles achieve the same cancer treatment efficacy with only ⅓ of the taxane content when compared to larger nanoparticles. Thus, lower doses of drug can be used and the risk of side effects is minimized.

The taxane-induced aggregates also can be linked with a targeting moiety or group including, but not limited to, an antibody (or antigen-binding portion thereof), antigen, cognate carbohydrates (e.g., sialic acid), a cell surface receptor ligand, a moiety that binds a cell surface receptor, such as, prostate-specific membrane antigen (PSMA), a moiety that binds a cell surface saccharide, an extracellular matrix ligand, a cytosolic receptor ligand, a growth factor, a cytokine, an incretin, a hormone, a lectin, a lectin target, such as, a galactose, a galactose derivative, an N-acetylgalactosamine, a mannose, a mannose derivative and the like, a vitamin, such as, a folate, a biotin and the like, an avidin, a streptavidin, a neutravidin, a DNA, an RNA etc. to form a conjugate so that the targeting group(s) are incorporated with nanocomposite particle of interest (FIG. 10).

Drug Formulation and Nanoparticle Preparation

Taxane and modified homopolymer can be suspended individually in suitable buffers and/or solvents, such as, a buffer, methanol, acetone, ethanol and the like, at suitable concentrations, such as, those which are established for in vivo use, generally in milligram or nanogram quantities. Then, the two solutions are mixed at a suitable temperature, such as, room temperature or at another temperature known to be acceptable for maintaining integrity of the taxane and homopolymer, for a suitable period of time, such as, one hour, two hours and so on. Other incubation times can vary from minutes to hours as the aggregates of interest are stable once formed. The aggregates can be concentrated or collected practicing methods known in the art, for example, by filtration, centrifugation, evaporation, lyophilization, dialysis and the like. The aggregates can be desiccated for extended shelf life.

For example, a taxane, such as, paclitaxel, was dissolved in methanol or ethanol in various amounts of up to 40 mg/mL. A hydrocarbon ($CH_3(CH_2)_{17}$)-modified randomly branched PEOX60 (monomer to initiator molar ratio=60:1) was prepared as taught herein and dissolved at varying concentrations of up 100 mg/mL in methanol or ethanol.

The two solutions then were mixed in various volumes to result in final homopolymer to taxane weight ratios in the mixtures ranging from 2:1 to 10:1 and rotary evaporated to dryness. The mixtures then were redissolved in water or saline, followed by sterile filtration by a 0.22 μM filter and lyophilization for 20 to 72 hours depending on volume to yield a dry powder.

The size of the aggregates or nanoparticles, as measured by light scattering, can range from about 50 to about 100 nm, from about 60 to about 95 nm and from about 70 to about 90 nm (e.g., at 3 mg paclitaxel per mL) before lyophilization. The size of aggregates can range from about 110 to about 150 nm, from about 115 to about 145 nm, from about 120 to about 140 nm (e.g., at 5 mg paclitaxel per mL) in diameter after lyophilization.

In an aspect, the invention is directed to an aggregate comprising:
a) a polyoxazoline comprising at least one first terminal group modified with a hydrophobic moiety, wherein the polyoxazoline further comprises a linear portion, a branched portion or both, and the branched portion comprises a symmetrically branched polymer, an asymmetrically branched polymer or a combination thereof; and the polyoxazoline comprises a molar ratio of monomer to initiator in a range of from 50:1 to 80:1, and
b) a taxane,
wherein the polyoxazoline and the taxane comprises a weight ratio of polymer to taxane of 6:1 to 8:1, and the aggregate is from about 50 nm to about 100 nm in size, and
wherein the aggregate comprises a filtration rate through a 0.22 μm filter of from 50 to 100 percent.

Any aforementioned polyoxazoline polymer can be suitable. The aggregate can be formed as described herein.

Filtration rate of the polymer-drug aggregates through a filter of known pore size can be measured according to following procedure:
a polymer-drug aggregate sample can be dissolved in water, saline, PBS, or a solvent as described herein at a predetermined final concentration. Based on filter composition, a polymer-aggregate can be dissolved in water, saline, PBS, other aqueous solution, a solvent and so on. In an example, a polymer-drug aggregate sample is prepared based on weight of the polymer. In an example, a polymer-drug aggregate sample is prepared based on weight of the drug, such as, paclitaxel. In an example, a polymer-drug aggregate sample is prepared based on a final paclitaxel concentration, such as, mg/mL.

A sample can be passed through the filter by, for example, gravity or by pressure. It is common for pressure to be applied to compel a sample to pass through a filter. An optional pressure gauge can be used. In an example, a container is sealed and a sample is exposed to pressurized air. In embodiments, a sealed container is configured to accept a vacuum in a collection portion of the sealed container to draw sample through an integral filter.

In an example, a syringe with a plunger is used in conjunction with a filter assembly which interfaces with the nozzle portion of the syringe. A sample is loaded into the barrel of the syringe and the sample therein is forced to pass through the filter assembly by depressing the plunger of the syringe with pressure. A constant pressure is applied to the plunger until all of the sample is expelled from the barrel. If filter clogging occurs which is evident by back pressure and reduced passage of fluid through the filter into the collection portion of the device or a collection vessel, pressure is removed as excessive pressure on the plunger can rupture the membrane or can disrupt the assembly.

A predetermined volume, $V_0$, of a sample is loaded into a container. Then, the container is attached or is exposed to a filter assembly. For a 0.22 μm filter assembly, a $V_0$ of 9-10 ml can be selected. Any sample volume remaining in the container, $V_1$, is recorded. Filtered volume, $V_f$, can be calculated with the formula, $V_f=V_0-V_1$. Alternatively, $V_f$ can be determined by measuring the volume of the filtrate or of the collected filtered sample.

Filtration rate, $R_f$, of a sample can be calculated with the formula: $R_f=V_f/V_0$.

$R_f$ can be expressed as a fraction or the fraction can be converted to a percentage by multiplying the fraction by 100.

It has been discovered that polymer-drug aggregates prepared from, for example, $C_{18}$-PEOXABP60 and paclitaxel, unexpectedly can be passed through a 0.22 μm filter with a filtration rate of 50%-100%. As a comparison, polymer-drug aggregates prepared from $C_{18}$-PEOXABP100 and paclitaxel only have a filtration rate of less than 50%.

In embodiments, a filtration rate must be at least 50%, at least 60%, at least 70%, at least 80%, at least 90% or more; must be in a range of 50-100%, 60-100%, 70-100%, 80-100%, 90-100%, 55-100%, 65-100%, 75-100%, 85-100%, 95-100%, 55-95%, 65-95%, 75-95%, 85-95%, 50-95%, 60-95%, 70-95%, 80-95%, 90-95%, 50-90%, 60-90%, 70-90%, 80-90%, 55-90%, 65-90%, 75-90%, 85-90%; or, in any rate, must be 50% or greater.

Since polymer-drug aggregates, in embodiments, are intended for pharmaceutical use, and sterilization by filtration through a 0.22 μm filter is a common processing requirement or step, such a discovery of the correlation between monomer:initiator ratio and polymer:drug ratio, and aggregate size provides advantages at least for ease of manufacturing and reducing waste.

Selection of specific monomer to initiator molar ratios and specific polymer:drug ratios to yield certain sized aggregates is unexpected and surprising. Polyoxazoline polymers with lower monomer to initiator molar ratios, such as, $C_{18}$-PEOXABP20, are unsuitable for drug formulation due to manufacturing limitations and variations in cytotoxicity in some cell bioassays. Polymers with a monomer to initiator molar ratio of from about 50:1 to 80:1 provide drug aggregates comprising ease of manufacturing, reduced cytotoxicity and high filtration rate using a 0.22 μm filter.

The first terminal group modified with a hydrophobic moiety of the polyoxazoline polymer can comprise a hydrophobic electrophilic molecule including hydrocarbons, aliphatic hydrocarbons, aromatic hydrocarbons or a combination of both, along with a halide functional group, such as, alkyl halides, aralkyl halides, acyl halides or combinations thereof and can be provided by an initiator. Polymerization of an initiator and one or more monomers of choice can produce a polyoxazoline of this invention having at least one first terminal group modified with a hydrophobic moiety. As disclosed throughout this application, the initiator can comprise a hydrophobic electrophilic molecule including a hydrocarbon. The hydrocarbon can comprise from 1 to about 22 carbons, which may be saturated or unsaturated. In one embodiment, the initiator can comprise an aliphatic hydrocarbon, an aromatic hydrocarbon or a combination of both. The initiator can comprise a halide functional group. In one example, the initiator can comprise an alkyl halide, an aralkyl halide, an acyl halide or combination thereof.

The initiator can comprise alkyl halides containing from 1 to about 22 carbons, including, but not limited to, methyl iodide, methyl bromide, methyl chloride, ethyl iodide, ethyl bromide, ethyl chloride, 1-iodopropane, 1-bromopropane, 1-chloropropane, 1-iodobutane, 1-bromobutane, 1-chlorobutane, 1-iodopentane, 1-bromopentane, 1-chloropentane, 1-iodo hexane, 1-bromo hexane, 1-chloro hexane, 1-iodo dodecane, 1-bromo dodecane, 1-chloro dodecane, 1-iodo octadodecane, 1-bromo octadodecane, 1-chloro octadodecane, as well as benzyl iodide, benzyl bromide, benzyl chloride, allyl bromide, acyl iodide, acyl bromide, acyl chloride, benzoyl bromide or benzoyl chloride. In a further example, the initiator comprises a tosyl group.

As disclosed herein, the phrase, "polyoxazoline comprises a molar ratio of monomer to initiator in a range of from," means that the polyoxazoline is produced by reacting an initiator and at least one monomer at a monomer to initiator ratio (molar ratio) in that specific range including the starting and the ending points. Monomers, such as, oxazoline and substituted oxazoline disclosed herein can be suitable. Initiators disclosed above and hereafter can be suitable.

The aggregate can comprise a size from 50 nm to about 100 nm before lyophilization. The term, "size," refers to a size of particles of the polymer-drug aggregate in solution as measured using dynamic light scattering method described hereafter. The size of the polymer-drug aggregate can be the size measured in an aqueous solution in one example, in water, in another example, in saline, in yet another example, in a buffer, such as, a phosphate buffer (PBS), in yet another example, in a combination of saline and buffer in a further example.

In the aggregate of this invention, the polyoxazoline can further comprise a second terminal group comprising a functional group modified by an ethylenediamine (EDA) or an ethylenediamine derivative thereof. The ethylenediamine derivative can comprise diethylenetriamine, triethylenetetramine, tetraethylenepentamine, pentaethylenehexamine, polyethylene amine or tetramethylethylenediamine.

In the aggregate of this invention disclosed herein, the taxane can be associated with the at least one first terminal group modified with a hydrophobic moiety. The taxane can be associated with the first terminal group via a covalent bond, a non-covalent link, or a combination thereof. In one example, the taxane is associated with the hydrocarbon via a non-covalent link. Not wishing to be bound by a particular theory or mechanism, Applicants believe that hydrophobicity of the hydrocarbon of the polyoxazoline provides desired interaction between the polymer and taxane, which is water insoluble or poorly water soluble.

The aggregate disclosed herein can further comprise a targeting moiety. The targeting moiety can comprise an antibody, an antigen binding portion thereof, an antigen, a cell surface receptor, a cytosolic receptor, a cell receptor ligand or a lectin ligand.

The polyoxazoline of this invention can comprise poly (2-oxazoline), poly(2-substituted oxazoline) or a combination thereof. In one example, the polyoxazoline can comprise poly(2-methyloxazoline), poly(2-ethyloxazoline), poly (2-propyloxazoline), poly(2-butyloxazoline) or a combination thereof. The polyoxazoline of this invention can be polymerized from at least one monomer comprising oxazoline, 2-substituted oxazoline, or a combination thereof. The oxazoline can be 2-oxazoline. The 2-substituted oxazoline can comprise 2-methyloxazoline, 2-ethyloxazoline, 2-propyloxazoline, 2-butyloxazoline or a combination thereof.

In the aggregate of this invention, the taxane can comprise paclitaxel, docetaxel or a combination thereof.

The aggregate of this invention can be sterile. In one example, the aggregate can be sterilized by filtration through a 0.22 μm filter.

This invention is further directed to a pharmaceutical composition comprising an aggregate disclosed herein. In embodiments, the pharmaceutical composition comprises an aggregate comprising:

a) a polyoxazoline comprising at least one first terminal group modified with a hydrophobic moiety, wherein the polyoxazoline further comprises a linear portion, a branched portion or both, and the branched portion comprises a symmetrically branched polymer, an asymmetrically branched polymer or a combination thereof; and the polyoxazoline comprises a molar ratio of monomer to initiator in a range of, for example, from 50:1 to 80:1, and b) a taxane, wherein the polyoxazoline and the taxane has a weight ratio of polymer to taxane of, for example, 6:1 to 8:1, and the aggregate is from about 50 nm to about 100 nm in size, and wherein the aggregate has a filtration rate through a 0.22 μm filter in a range of from 50 to 100 percent.

A polyoxazoline as known or described herein can be suitable polymer. The initiator for the polyoxazoline can comprise a hydrophobic electrophilic molecule, for example, a hydrocarbon, such as, an aliphatic hydrocarbon, an aromatic hydrocarbon or a combination of both. The hydrocarbon can comprise from 1 to about 22 carbons, which may be saturated or unsaturated. The initiator can comprise a halide functional group, an alkyl halide, an aralkyl halide, an acyl halide or combination thereof. In one example, the initiator can comprise methyl iodide, methyl bromide, methyl chloride, ethyl iodide, ethyl bromide, ethyl chloride, 1-iodopropane, 1-bromopropane, 1-chloropropane, 1-iodobutane, 1-bromobutane, 1-chlorobutane, 1-iodopentane, 1-bromopentane, 1-chloropentane, 1-iodo hexane, 1-bromo hexane, 1-chloro hexane, 1-iodo dodecane, 1-bromo dodecane, 1-chloro dodecane, 1-iodo octadodecane, 1-bromo octadodecane, 1-chloro octadodecane, benzyl iodide, benzyl bromide, benzyl chloride, allyl bromide, acyl iodide, acyl bromide, acyl chloride, benzoyl bromide, benzoyl chloride or a combination thereof. In a further example, the initiator comprises a tosyl group. The polyoxazoline can further comprise a second terminal group comprising a functional group modified by EDA or an ethylenediamine derivative thereof, wherein the ethylenediamine derivative comprises diethylenetriamine, triethylenetetramine, tetraethylenepentamine, pentaethylenehexamine, polyethylene amine or tetramethylethylenediamine. The polyoxazoline can comprise poly(2-oxazoline), poly(2 substituted oxazoline) or a combination thereof. In a particular example, the polyoxazoline can comprise poly(2-methyloxazoline), poly (2-ethyloxazoline), poly(2-propyloxazoline) or poly(2-butyloxazoline) or a combination thereof.

In the pharmaceutical composition, the aggregate can comprise particles having a size from 50 nm to about 100 nm before lyophilization.

In the pharmaceutical composition, the taxane can be associated with said at least one first terminal group.

The aggregate can further comprise a targeting moiety, wherein the targeting moiety can comprise an antibody, an antigen binding portion thereof, an antigen, a cell surface receptor, a cytosolic receptor, a cell receptor ligand or a lectin ligand, as disclosed above.

In the pharmaceutical composition, the taxane can comprise paclitaxel, docetaxel or a combination thereof.

The pharmaceutical composition can further comprise a carrier. Carriers disclosed herein can be suitable.

The pharmaceutical composition can be a cancer treatment drug for treating breast cancers, ovarian cancers, lung cancers, an NSCLC (Non-Small Cell Lung Cancer), colon cancers, gastric cancers, melanomas, head and neck cancers, pancreatic cancers or a combination thereof. In pharmaceutical composition can be administered to a patient via parenteral, e.g., intravenous, intradermal, subcutaneous, oral (e.g., inhalation), transdermal (topical), transmucosal or rectal administration, or a combination thereof.

It was discovered that unexpectedly polyoxazoline polymers polymerized with a specific range of monomer to initiator molar ratio provide an advantage in filtration for the manufacturing: polymers having monomer to initiator molar ratios in a range of from 50:1 to about 80:1, such as, $C_{18}$-PEOXABP60, can produce polymer-drug aggregates that can pass through a 0.22 µm membrane filter with an $R_f$ of about 50% to 100% for producing sterile drug aggregate preparations, while polymers having monomer to initiator molar ratios of, for example, 100:1 ($C_{18}$-PEOXABP100) or greater produce polymer-drug aggregates that have a filtration rate of less than 50%. Such a low filtration rate leads to lower yield of product, material waste and longer filtration process resulting in reduced productivity for manufacturing.

Not wishing to be bound by any particular theory or mechanism, it is believed polymer-drug aggregates produced from a polymer having a monomer to initiator molar ratio of 100:1 or greater have undesirable aggregate size and aggregate distribution, and are susceptible to inter-particle interaction, particle-filter interaction, or a combination thereof, so when particles are forced into proximity or close to filter materials, such as, when passed through a 0.22 µm filter under pressure, aggregates may further aggregate or interact causing the filter to be clogged leading to a lower filtration rate. Unexpectedly, it was discovered that a monomer to initiator molar ratio, for example, in the 50:1 to 80:1 range overcomes the filter clogging problem leading to easier manufacturing, reduced waste and increased productivity.

A pharmaceutical composition of this disclosure for use as disclosed herein is formulated to be compatible with intended routes of administration. Examples of routes of administration can include parenteral, e.g., intravenous, intradermal, subcutaneous, oral (e.g., inhalation), transdermal (topical), transmucosal and rectal administration. Solutions or suspensions used for parenteral, intradermal or subcutaneous application can include a sterile diluent, such as, water for injection, saline, oils, polyethylene glycols, glycerine, propylene glycol or other synthetic solvents; antibacterial agents, such as, benzyl alcohol or methyl parabens; antioxidants, such as, ascorbic acid or sodium bisulfite; chelating agents, such as, EDTA; buffers, such as, acetates, citrates or phosphates; and agents for the adjustment of tonicity, such as, sodium chloride or dextrose. pH can be adjusted with acids or bases, such as, HCl or NaOH. The parenteral preparation can be enclosed in ampoules, disposable syringes or multiple dose vials made of glass or plastic as an article of manufacture.

Pharmaceutical compositions suitable for injectable use include sterile aqueous solutions or dispersions and sterile powders for the extemporaneous preparation, of sterile injectable solutions or dispersions. For intravenous administration, suitable carriers include physiological saline, bacteriostatic water or phosphate-buffered saline (PBS). The composition generally is sterile and is fluid to the extent that syringability exists. The composition must be stable under the conditions of manufacture and storage and must be preserved against the contaminating action of microorganisms, such as, bacteria and fungi. The carrier can be a solvent or dispersion medium containing, for example, water, ethanol, polyol (for example, glycerol, propylene glycol, liquid PEG, polysorbates and the like) and suitable mixtures thereof. Proper fluidity can be maintained, for example, by use of a coating, such as, a lecithin, by maintenance of required particle size in the case of dispersion, use of a thickener and by use of surfactants. Prevention of action of microorganisms can be achieved by various antibacterial and antifungal agents, for example, parabens, chlorobutanol, phenol, ascorbic acid and the like. Isotonic agents, for example, sugars, polyalcohols, such as, mannitol, sorbitol or sodium chloride, can be included in the composition. Prolonged absorption of injectable compositions can be brought about by including in the composition, an agent that delays absorption, for example, aluminum monostearate or gelatin.

Sterile injectable solutions can be prepared by incorporating active compound in the required amount of an appropriate solvent with one or a combination of ingredients enumerated above, as required, followed by filter sterilization. Generally, dispersions are prepared by incorporating an active compound in a sterile vehicle that contains a basic dispersion medium and the required other ingredients, for example, from those enumerated above, and as known in the art. In the case of sterile powders for preparation of sterile injectable solutions, the preparation can be treated by, for example, lyophilization, vacuum drying or freeze drying, that yields a powder of the active ingredient plus any additional desired ingredient from a previously sterile-filtered solution thereof. A preparation of interest can be stored and reconstituted with a suitable liquid for use.

Oral compositions generally include an inert diluent, flavorant, odorant or an edible carrier. The composition can be enclosed in gelatin capsules or compressed into tablets. For the purpose of oral therapeutic administration, the active compound can be incorporated with excipients and used in the form of tablets, troches or capsules. Oral compositions also can be prepared using a fluid carrier to yield a syrup or liquid formulation, or for use as a mouthwash, wherein the compound in the fluid carrier is applied orally and swished and expectorated or swallowed.

Pharmaceutically compatible binding agents and/or adjuvant materials can be included, as part of the composition. Tablets, pills, capsules, troches and the like can contain a binder, such as, microcrystalline cellulose, gum tragacanth or gelatin; an excipient, such as, starch or lactose, a disintegrating agent, such as, alginic acid, PRIMOGEL® (a modified corn starch, a trademark of DFE pharma, DE) or corn starch; a lubricant, such as, magnesium stearate or Sterotes (U.S. Pat. No. 8,933,193); a glidant, such as, colloidal silicon dioxide; a sweetening agent, such as, sucrose or saccharin; or a flavoring agent, such as, peppermint, methyl salicylate or orange flavoring.

For administration by inhalation, the compound is delivered in the form of, for example, a wet or dry aerosol spray from a pressurized container or dispenser that contains a suitable propellant, e.g., a gas, such as, carbon dioxide or a nebulizer, or a mist.

Systemic administration also can be by transmucosal or transdermal means. For transmucosal or transdermal administration, penetrants appropriate to the barrier to be permeated are used in the formulation. Such penetrants generally are known in the art and include, for example, for transmucosal administration, detergents, bile salts and fusidic acid derivatives. Transmucosal administration can be accomplished through the use of nasal sprays or suppositories. For transdermal administration, the active compounds are formulated into ointments, salves, gels or creams as generally known in the art. A suitable carrier includes dimethylsulfoxide.

The compound also can be prepared in the form of suppositories (e.g., with conventional suppository bases, such as, cocoa butter and other glycerides) or retention enemas for rectal delivery.

In one embodiment, the active compound is prepared with carriers that will protect the compound against rapid elimination from the body, such as, a controlled release formulation, including implants and microencapsulated delivery systems. Biodegradable, biocompatible polymers can be used, such as, ethylene vinyl acetate, polyanhydrides, polyglycolic acid, collagen, polyorthoesters and polylactic acid.

Methods for preparation of such formulations will be apparent to those skilled in the art. The materials also can be obtained commercially, for example, from Alza Corporation and Nova Pharmaceuticals, Inc.

The instant aggregates can be used in topical forms, such as, creams, ointments, lotions, unguents, other cosmetics and the like. Pharmaceutically active agents (PAAs), such as, the taxanes of interest and other bioactive or inert compounds, can be carried, and include emollients, bleaching agents, antiperspirants, pharmaceuticals, moisturizers, scents, colorants, pigments, dyes, antioxidants, oils, fatty acids, lipids, inorganic salts, organic molecules, opacifiers, vitamins, pharmaceuticals, keratolytic agents, UV blocking agents, tanning accelerators, depigmenting agents, deodorants, perfumes, insect repellants and the like.

It can be advantageous to formulate oral or parenteral compositions in dosage unit form for ease of administration and uniformity of dosage. "Dosage unit form," as used herein refers to physically discrete units suited as unitary dosages for a subject to be treated; each unit containing a predetermined quantity of active compound calculated to produce a desired therapeutic endpoint.

The dosages, for example, preferred routes of administration and amounts are obtainable based on empirical data obtained from preclinical and clinical studies, practicing methods known in the art. The dosage and delivery form can be dictated by and can be dependent on the characteristics of the PAA, the polymer, the particular therapeutic effect to be achieved, the characteristics and condition of the recipient and so on. For repeated administrations over several days or longer, depending on the condition, the treatment can be sustained until a desired endpoint is attained. An exemplary dosing regimen is disclosed in WO 94/04188.

The progress of the therapy can be monitored by conventional techniques and assays, as well as patient input.

The pharmaceutical compositions can be included in a container, pack or dispenser together with instructions for administration.

Another method of administration comprises the addition of a compound of interest into or with a food or drink, as a food supplement or additive, or as a dosage form taken on a prophylactic basis, similar to a vitamin. The aggregate of interest can be encapsulated into forms that will survive passage through the gastric environment. Such forms are commonly known, for example, enteric coated formulations. Alternatively, the aggregate of interest can be modified to enhance half-life, such as, chemical modification or combination with agents known to result in delayed, sustained or controlled release, as known in the art.

The instant disclosure now will be exemplified in the following non-limiting examples.

EXAMPLES

The present invention is further defined in the following Examples. It should be understood that the Examples, while indicating embodiments of the invention, are given by way of illustration only. From the above discussion and the Examples, one skilled in the art can ascertain the essential characteristics of the invention, and without departing from the spirit and scope thereof, can make various changes and modifications of the invention to adapt to various uses and conditions.

Materials

Symmetrically branched PPI dendrimers were purchased from Sigma-Aldrich. Symmetrically branched PEI dendrimers and dendrigrafts were prepared according to procedures provided in U.S. Pat. Nos. 4,631,337, 5,773,527, 5,631,329 and 5,919,442. All of the antibodies were purchased from Sigma-Aldrich, Biodesign or Fitzgerald. Different generation PAMAM dendrimers were purchased from Dendritech, Inc.

Modified Symmetrically Branched PPIs with Amino Functional Groups (m-SB-PPI-$NH_2$-1.0)

The following reagents, including symmetrically branched PPI (SB-PPI-4, 8, 16, 32, 64, MW 316, 773, 1,687, 3,514 and 7,168), methyl acrylate (MA, FW=86.09), EDA (FW=60.10) and methanol, were utilized.

To a round bottom flask were added 1.0 g PPI-64 dendrimer (MW 7168) and 20 ml methanol (solution A). To a separate round bottom flask were added 2.4 g methylacrylate (MA) and 10 ml methanol (solution B). Solution A was then slowly dropped into solution B while stirring at room temperature. The resulting solution was allowed to react at 40° C. for 2 hours. On completion of the reaction, the solvent and unreacted MA monomer were removed by rotary evaporation and the product, 2.5 g of MA-functionalized PPI, then was redissolved in 20 ml of methanol.

To a round bottom flask were added 160 g EDA and 50 ml of methanol, followed by a slow addition of MA-functionalized PPI at 0° C. The solution then was allowed to react at 4° C. for 48 hours. The solvent and the excess EDA were removed by rotary evaporation. The crude product then was precipitated from an ethyl ether solution and further purified by dialysis to give about 2.8 g of primary amine-functionalized symmetrically branched PPI (m-SB-PPI-$NH_2$-1.0) with a molecular weight of about 21,760. The product was characterized by $^1H$ and $^{13}C$ nuclear magnetic resonance (NMR) and size exclusion chromatography (SEC).

Other MA or primary amine-modified symmetrically branched PPI dendrimers and symmetrically branched PEI dendrigrafts with various molecular weights were prepared in a similar manner.

Modified Symmetrically Branched PPIs with Mixed Hydroxyl and Amino Functional Groups (Mix-m-SB-PPI-64-$NH_2$/OH-2)

Amino-functionalized symmetrically branched PPI (m-SB-PPI-64-NH$_2$-1.0), MA, EDA, monoethanolamine (MEA, FW=61.08) and methanol were utilized.

To a round bottom flask were added 1.0 g amino-modified. PPI or m-SB-PPI-NH$_2$-1.0 produced from the previous procedure and 20 ml of methanol (solution A). To a separate round bottom flask were added 2.4 g of MA and 10 ml methanol (solution B). Solution A then was dripped slowly into solution B while stirring at room temperature. The resulting solution was allowed to react at 40° C. for 2 hours. On completion of the reaction, the solvent and unreacted monomer MA were removed by rotary evaporation and. the product, 2.5 g of MA-functionalized m-SB-PPI-64-MA-1.5, then was redissolved in 20 ml of methanol.

To a round bottom flask were added 32 g EDA, 130 g MEA and 100 ml methanol (the molar ratio of EDA:MEA was 20:80), followed by slow addition of m-SB-PPI-64-MA-1.5 at 0° C. The solution then was allowed to react at 4° C. for 48 hours. The solvent and the excess EDA were removed by rotary evaporation. The crude product then was precipitated from an ethyl ether solution and further purified by dialysis to give about 2.8 g of mixed hydroxyl and amino functionalized (mixed surface) SBP (mix-m-SB-PPI-64-NH$_2$/OH-2.0, with an average of 20% NH$_2$ and 80% OH surface groups and a molecular weight of about 21,862).

Other modified random AB-PEI and regular AB-PLL molecules with varying ratios of hydroxyl and amino groups, as well as different molecular weights, were prepared in a similar manner.

Random asymmetrically branched PEI's were purchased from Aldrich and Polysciences. Regular ABP's were prepared according to procedures provided in U.S. Pat. No. 4,289,872. All of the antibodies were purchased from Sigma-Aldrich, Biodesign or Fitzgerald.

Modified Random Asymmetrically Branched PEI's with Amino Functional Groups (m-Ran-AB-PEI-NH$_2$-1.0)

Random asymmetrically branched PEI (ran-AB-PEI, MW 2,000, 25,000 and 75,000), MA, EDA and methanol were utilized.

To a round bottom flask were added 1.0 g PEI (MW 2,000) and 20 ml methanol (solution A). To a separate round bottom flask were added 3.0 g MA and 10 ml methanol (solution B). Solution A then was dripped slowly into solution B while stirring at room temperature. The resulting solution was allowed to react at 40° C. for 2 hours. On completion of the reaction, the solvent and unreacted MA were removed by rotary evaporation and the product, MA-functionalized PEI, then was redissolved in 20 ml of methanol.

To a round bottom flask were added 80 g EDA and 50 ml of methanol, followed by a slow addition of MA-functionalized PEI at 0° C. (1 g MA dissolved in 20 ml methanol). The solution then was allowed to react at 4° C. for 48 hours. The solvent and excess EDA were removed by rotary evaporation. The crude product then was precipitated from an ethyl ether solution and further purified by dialysis to give about 3.0 g of primary amine-functionalized random asymmetrically branched PEI (m-ran-AB-PEI-NH$_2$-1.0) with a molecular weight of about 7,300. The product was characterized by $^1$H and $^{13}$C NMR and SEC.

Other MA or primary amine modified random asymmetrically branched PEI and regular asymmetrically branched PLL polymers with various molecular weights were prepared in a similar manner.

Modification of Branched Polymers with Hydrocarbon Chains

The modification of a randomly branched PEI with 10% hydrocarbon chains is used as an example. One gram of branched PEI (FW=25000) was dissolved in 10 mL methanol. To the solution were added 0.23 g of 1,2-epoxyhexane (FW=100.16) and the mixture was heated at 40° C. for 2 hours. The solvent then was rotary evaporated and the residue redissolved in water. After dialysis (3,500 cutoff), the modified PEI was generated.

Other MBP's, such as, PAMAM, PEI and PPI dendrimers and dendrigrafts, and asymmetric PLL with various percentages and lengths (e.g., $C_4$, $C_{12}$, $C_{18}$ and $C_{22}$) of hydrocarbon chains were prepared in a similar manner.

Modified Random Asymmetrically Branched PEI's with Mixed Hydroxyl and Amino Functional Groups (m-Ran-AB-PEI-NH$_2$/OH-2)

Amino-functionalized random asymmetrically branched PEI (m-ran-AB-PEI-NH$_2$-1.0), MA, EDA, monoethanolamine (MEA, FW=61.08) and methanol were utilized.

To a round bottom flask were added 1.0 g amino-modified PEI or m-ran-AB-PEI-NH$_2$-1.0 produced from the previous procedure and 20 ml of methanol (solution A). To a separate round bottom flask were added 3.0 g of MA and 10 ml methanol (solution B). Solution A then was slowly dripped into solution B while stirring at room temperature. The resulting solution was allowed to react at 40° C. for 2 hours. On completion of the reaction, the solvent and unreacted MA were removed by rotary evaporation and the product, MA-functionalized m-ran-AB-PEI-MA-1.5, then was redissolved in 20 ml of methanol.

To a round bottom flask were added 60 g EDA, 244 g MEA and 100 ml methanol (the mole ratio of EDA:MEA was 20:80), followed by slow addition of m-ran-AB-PEI-MA-1.5 at 0° C. (1 g MA dissolved in 20 ml of methanol). The solution then was allowed to react at 4° C. for 48 hours. The solvent and excess EDA were removed by rotary evaporation. The crude product then was precipitated from an ethyl ether solution and further purified by dialysis to give about 2.4 g of mixed hydroxyl and amino functionalized random ABP (m-ran-AB-PEI-NH$_2$/OH-2.0, with an average of 20% NH$_2$ and 80% OH surface groups and the molecular weight was about 18,000).

Other modified random AB-PEI and regular AB-PLL polymers with various ratios of hydroxyl and amino groups, as well as different molecular weights were prepared in a similar manner.

Alkyl-Modified Random Asymmetrically Branched Poly(2-Ethyloxaxoline) (PEOX) with Primary Amine Chain End Group The synthesis of CH$_3$—(CH$_2$)$_{11}$-PEOX-ABP100 (C$_{12}$ABP100 is an arbitrary name to denote the molar ratio of monomer to initiator in the initial reaction) is provided as a general procedure for the preparation of core shell structures. A mixture of CH$_3$(CH$_2$)$_{11}$—Br (2.52 g) in 500 ml of toluene was azeotroped to remove water with a distillation head under N$_2$ for about 15 min. 2-Ethyloxazoline (100 g) was added dropwise through an addition funnel and the mixture was allowed to reflux between 24 and 48 hours. On completion of the polymerization, 12.12 g of EDA were added to the reactive polymer solution (A) to introduce the amine function group. The molar ratio of PDX chain end to EDA was 1 to 20.

Alternatively, N-Boc-piperazine or water (e.g., with 1N Na$_2$CO$_3$) can be added to terminate the reaction. Morpholine or PEI also can be added to the reactive polymer solution (A) to terminate the reaction. The crude product was redissolved in methanol and then precipitated from a large excess of diethyl ether. The bottom layer was redissolved in methanol and dried by rotary evaporation and vacuum to give an asymmetrically random branched PEOX polymer as a white solid (101 g).

Other asymmetrically randomly branched polymers, such as, $C_6$-PEOX ABP20, 50, 100, 200, 300 and 500, $C_{12}$-PEOX ABP20, 50, 200, 300 and 500, $C_{22}$-PEOX ABP20, 50, 100, 200, 300 and 500, and polystyrene-PEOX etc., as well as, non-modified and modified poly(2-substituted oxazoline), such as, poly(2-methyloxazoline), were prepared in a similar manner. All the products were analyzed by SEC and NMR.

Alkyl-Modified Random Asymmetrically Branched Poly(2-Ethyloxazoline) (PEOX) with Primary Amine Chain End Group The synthesis of $CH_3$—$(CH_2)_{17}$-PEOX-ABP60 ($C_{18}$-PE-OXABP60 is an arbitrary name to denote the molar ratio of monomer to initiator in the initial reaction) is provided as a general procedure for the preparation of core shell structures. A mixture of $CH_3(CH_2)_{17}$—Br (5.61 g) in 500 ml of toluene was azeotroped to remove water with a distillation head under $N_2$ for about 15 min. 2-Ethyloxazoline (100 g) was added dropwise through an addition funnel and the mixture was allowed to reflux between 24 and 48 hours. On completion of the polymerization, 10.1 g of EDA were added to the reactive polymer solution (A) to introduce the amine function group. The molar ratio of polyoxazoline reactive chain end to EDA was 1 to 10.

Alternatively, N-Boc-piperazine or water (e.g., with 1N $Na_2CO_3$) can be added to terminate the reaction. Morpholine or PEI also can be added to the reactive polymer solution (A) to terminate the reaction. The crude product was redissolved in methanol and then precipitated from a large excess of diethyl ether. The bottom layer was redissolved in methanol and dried by rotary evaporation and vacuum to give an asymmetrically random branched PEOX polymer as a white solid.

Other asymmetrically randomly branched polymers, such as, $C_{18}$-PEOX ABP20, 40, 50, 70, 80, 100, 120, 200, 300, 500 etc. as well as, non-modified and modified poly(2-substituted oxazoline), such as, poly(2-methyloxazoline), were prepared in a similar manner. All the products were analyzed by SEC and NMR.

Mixed Surface Modified Symmetrical Branched Polymer-IgG Conjugates

The preparation of mixed surface ($OH/NH_2$ mix) modified symmetrically branched PPI-IgG conjugates (mix-m-SB-PPI-64-$NH_2$/OH-2-IgG conjugates) is provided as a general procedure for the preparation of polymer antibody.

Other conjugates, such as, m-SB-PPI-4-$NH_2$-1-IgG, m-SB-PPI-8-$NH_2$-1-IgG, m-SB-PPI-16-$NH_2$-1-IgG, m-SB-PPI-32-$NH_2$-1-IgG, m-SB-PPI-4-$NH_2$-2-IgG, m-SB-PPI-8-$NH_2$-2-IgG, m-SB-PPI-16-$NH_2$-2-IgG, m-SB-PPI-32-$NH_2$-2-IgG, m-SB-PPI-4-$NH_2$-3-IgG, m-SB-PPI-8-$NH_2$-3-IgG, m-SB-PPI-16-$NH_2$-3-IgG, m-SB-PPI-32-$NH_2$-3-IgG, mix-m-SB-PPI-4-$NH_2$/OH-1 ($OH/NH_2$ mix)-IgG, mix-m-SB-PPI-8-$NH_2$/OH-1 ($OH/NH_2$ mix)-IgG, mix-m-SB-PPI-16-$NH_2$/OH-1 ($OH/NH_2$ mix)-IgG, mix-m-SB-PPI-32-$NH_2$/OH-1 ($OH/NH_2$ mix)-IgG, mix-m-SB-PPI-4-$NH_2$/OH-2 ($OH/NH_2$ mix)-IgG, mix-m-SB-PPI-8-$NH_2$/OH-2 ($OH/NH_2$ mix)-IgG, mix-m-SB-PPI-16-$NH_2$/OH-2 ($OH/NH_2$ mix)-IgG, mix-m-SB-PPI-32-$NH_2$/OH-2 ($OH/NH_2$ mix)-IgG, mix-m-SB-PPI-4-$NH_2$/OH-3 ($OH/NH_2$ mix)-IgG, mix-m-SB-PPI-8-$NH_2$/OH-3 ($OH/NH_2$ mix)-IgG, mix-m-SB-PPI-16-$NH_2$/OH-3 ($OH/NH_2$ mix)-IgG, mix-m-SB-PPI-32-$NH_2$/OH-3 ($OH/NH_2$ mix)-IgG, as well as primary amine and mix $OH/NH_2$ modified Combburst PEI dendrigrafts (Generation 0-5) also were obtained in a similar manner. The synthesis of other targeting moieties attached to a modified SBP of interest also was obtained in a similar manner.

LC-SPDP-Mixed Surface m-SB-PPI-64-$NH_2$/OH-2

To the mixed surface randomly branched mix-m-SB-PPI-64-$NH_2$/OH-2 ($4\times10^{-7}$ mol) in 400 µl of phosphate buffer (20 mM phosphate and 0.1 M NaCl, pH 7.5) were added $4.0\times10^{-6}$ mol of sulfo-LC-SPDP (Pierce, IL) in 400 µL of water. The mixture was vortexed and incubated at 30° C. for 30 minutes. The LC-SPDP-mix-m-SB-PPI-64-$NH_2$/OH-2 was purified by gel filtration chromatography and equilibrated with buffer A (0.1 M phosphate, 0.1 M NaCl and 5 mM EDTA, pH 6.8). The product was concentrated further to yield 465 µL of solution with a concentration of approximately 0.77 nmol.

Thiolated Mix-m-SB-PPI-64-$NH_2$/OH-2

The LC-SPDP mix-m-SB-PPI-64-$NH_2$/OH-2 (50 nmol in 6511.1 of buffer A) was mixed with 100 µL of dithiothreitol (DTT) (50 mM in buffer A) and was incubated at room temperature for 15 minutes. Excess DTT and byproducts were removed by gel filtration with buffer A. The product was concentrated in a 10 K Centricon Concentrator to yield 390 µL of thiolated mix-m-SB-PPI-64-$NH_2$/OH-2 that was used for conjugation with activated antibody.

Maleimide R (MAL-R)-Activated Antibody

To the antibody in PBS (310 µL, 5.1 mg or 34 nmol) were added 20.4 µL of a MAL-R-NHS (N-hydroxysuccinimide) solution (10 mM in water). The mixture was vortexed and incubated at 30° C. for 15 minutes. The product was purified by gel filtration with buffer A. The maleimide-R-activated antibody was used for conjugation with the thiolated mix-m-SB-PPI-64-$NH_2$/OH-2.

Mix-m-SB-PPI-64-$NH_2$/OH-2-Antibody Conjugate

To the thiolated mix-m-SB-PPI-64-$NH_2$/OH-2 (310 µL or 35.7 nmol) was added the MAL-R-activated antibody (4.8 ml, or 34 nmol). The reaction mixture was concentrated to approximately 800 µL and then allowed to incubate overnight at 4° C. and/or at room temperature for about 1 hr. On completion, the reaction was quenched with 100 µL of ethyl maleimide (50 mM solution) and the conjugate then was fractionated on a carboxymethyl cellulose (CM cellulose) column (5 mL) with a sodium chloride step gradient in 20 mM phosphate buffer at pH 6. The conjugate was eluted with a sodium chloride gradient and characterized by cationic exchange chromatography, UV spectroscopy and polyacrylamide gel electrophoresis.

Conjugation Via Reductive Coupling-Reduction of Antibody

To the antibody, 2.1 mg or 14 nmol in 160 µL of buffer B (containing 0.1 M sodium phosphate, 5 mM EDTA and 0.1 M NaCl, pH 6.0) were added 40 µL of DTT (50 mM in buffer B). The solution was allowed to stand at room temperature for 30 min. The product was purified by gel filtration in a Sephadex G-25 column equilibrated with buffer B. The reduced antibody was concentrated to 220 µL and was used for conjugation.

MAL-R-Mixed Surface Modified SBP

To the mixed surface modified SBP in 400 µL ($400\times10^9$ mols) at pH 7.4 were added 400 µL of MAL-R-NHS (10 mM in water). That was mixed and incubated at 30° C. for 15 min. On termination, the product was purified on a Sephadex G-25 column equilibrated with buffer B. The MAL-R-mixed surface modified SBP was collected and stored in aliquots in the same buffer at −40° C.

Mixed Surface Modified SBP-Antibody Conjugate

To the reduced antibody (14 nmols in 220 µL) was added the MAL-R-mix-m-SB-PPI-64-$NH_2$/OH-2 (154 µL, 16.6 nmols) with stirring. The pH was adjusted to about 6.8 by the addition of 1.2.5 µL of sodium carbonate (1.0 M solution), the reaction was continued for 1 hr at room temperature and terminated with the addition of 100 µL of cysteamine (0.4 mM solution). The conjugation mixture was purified on a CM cellulose column with a sodium chloride gradient elution.

IgG-Asymmetrical Randomly Branched Polymer Conjugates

The preparation of randomly branched mixed surface (OH/$NH_2$ mix) m-ran-AB-PEI-$NH_2$/OH-2-IgG conjugates is provided as a general procedure for the preparation of polymer-antibody conjugates.

Other conjugates, such as, PEI-IgG, m-ran-AB-PEI-$NH_2$-1-IgG, m-ran-AB-PEI-$NH_2$-2-IgG, m-ran-AB-PEI-$NH_2$-3-IgG, m-ran-AB-PEI-$NH_2$-4-IgG, as well as m-ran-AB-PEI-$NH_2$/OH-1 (OH/$NH_2$ mix)-IgG, m-ran-AB-PEI-$NH_2$/OH-2 (OH/$NH_2$ mix)-IgG, m-ran-AB-PEI-$NH_2$/OH-3 (OH/$NH_2$ mix)-IgG, regular polylysine polymer, alkyl-modified randomly branched poly(2-ethyloxazoline) with primary amine chain ends were all synthesized in a similar manner. The synthesis of various protein conjugates with asymmetrically randomly branched PEOX polymers also is conducted in a similar manner.

LC-SPDP-Mixed Surface m-Ran-AB-PEI-$NH_2$/OH-2

To the mixed surface randomly branched m-ran-AB-PEI-$NH_2$/OH-2 ($4 \times 10^{-7}$ mol) in 400 µL of phosphate buffer (20 mM phosphate and 0.1 M NaCl, pH 7.5) were added $4.0 \times 10^{-6}$ mol of sulfo-LC-SPDP (Pierce, IL) in 400 µl of water. That was vortexed and incubated at 30° C. for 30 minutes. The LC-SPDP-m-ran-AB-PEI-$NH_2$/OH-2 was purified by gel filtration chromatography and equilibrated with buffer A (0.1 M phosphate, 0.1 M NaCl and 5 mM EDTA, pH 6.8). The product was concentrated further to yield 465 µl of solution with a concentration of approximately 0.77 nmol.

Thiolated m-Ran-AB-PEI-$NH_2$/OH-2

The LC-SPDP m-ran-AB-PEI-$NH_2$/OH-2 (50 nmol in 65 ml of buffer A) was mixed with 100 µL of dithiothreitol (DTT) (50 mM in buffer A) and was allowed to incubate at room temperature for 15 minutes. Excess DTT and byproducts were removed by gel filtration with buffer A. The product was concentrated in a 10 K Centricon Concentrator to yield 390 µL of the thiolated m-ran-AB-PEI-$NH_2$/OH-2 that was used for conjugation with activated antibody.

Maleimide-R-activated antibody made as described above was used for conjugation with the thiolated m-ran-AB-PEI-$NH_2$/OH-2.

m-Ran-AB-PEI-$NH_2$/OH-2-Antibody Conjugate

To the thiolated m-ran-AB-PEI-$NH_2$/OH-2 (310 µL or 35.7 nmol) was added the MAL-R-activated antibody (4.8 mL or 34 nmol). The reaction mixture was concentrated to approximately 800 µL and allowed to incubate overnight at 4° C. and/or at room temperature for about 1 hr. On completion, the reaction was quenched with 100 µL of ethyl maleimide (50 mM solution) and the conjugate then was fractionated on a CM cellulose column (5 ml) with a sodium chloride step gradient in 20 mM phosphate buffer at pH 6. The conjugate was eluted with a sodium chloride gradient and characterized by cationic exchange chromatography, UV spectroscopy and polyacrylamide gel electrophoresis.

Paclitaxel Formulation and Nanoparticle Preparation

As a general procedure, paclitaxel was dissolved in methanol to a concentration of up to 40 mg/mL. A $C_{18}$-PEOXABP60 polymer was separately dissolved to a concentration of up to 100 mg/mL in methanol. The two solutions were then mixed at various volumes to result in final polymer to paclitaxel weight ratios in the mixtures ranging from 3:1 to 10:1. The mixtures subsequently were lyophilized for 20 to 96 hours depending on volume.

The size of the aggregates as measured by light scattering ranged from about 70 nm to 90 nm in diameter before lyophilization and 120-140 nm after lyophilization.

Alternatively, both paclitaxel and the $C_{18}$-PEOXABP60 polymer can be dissolved in a common solvent, such as, acetone, methanol or ethanol, and then dropwise added to water while being stirred or sonicated, followed by sterile filtration with a 0.22 µm filter. The final product then can be generated by lyophilization and the size of the aggregates measured by light scattering.

Other taxane-induced aggregates or nanoparticles using various hydrophobically surface-modified branched polymers, such as, $C_4$, $C_6$, $C_{12}$ or $C_{22}$ hydrocarbon-modified randomly branched PEOX, PEI and PPI polymers: $C_4$, $C_6$, $C_{12}$, $C_{18}$ and $C_{22}$ hydrocarbon-modified PAMAM, PEI and PPI dendrimers and dendrigrafts; and $C_4$, $C_6$, $C_{12}$, $C_{18}$ and $C_{22}$ hydrocarbon-modified branched PLL/polymers can be prepared in a similar manner.

Nanoparticle with a 7:1 $C_{18}$-PEOXABP60 Polymer:Paclitaxel Ratio

Paclitaxel (700 mg) was dissolved in 9.33 mL of methanol to yield a 75 mg/mL solution. A 15 mg/mL solution of paclitaxel was also prepared by dissolving 100 mg in 6.67 mL of methanol. The two solutions were mixed for 20 minutes resulting in a solution containing 6.25 mg paclitaxel and 43.75 mg polymer per mL, providing a solution with a 7:1 polymer:drug ratio. The mixture was placed on a rotary evaporator and the methanol removed to dryness. The resultant solid was redissolved with stirring in 33.3 ml of water to a final paclitaxel concentration of 3 mg/mL. The solution preparation was passed through a 0.8 µm filter and then a 0.22 µm filter. The filtrate was lyophilized over a 24-72 hour period depending on the amount used. The vial was stoppered and the ready-to-use white powder was stored at room temperature. That preparation was designated as FID-007.

Nanoparticles with $C_{18}$-PEOXABP80 and $C_{18}$-PEOXABP50 and Paclitaxel

Polymers $C_{18}$-PEOXABP80 and $C_{18}$-PEOXABP50 were used to produce polymer-drug according to the same procedure described above at 7:1 polymer:drug ratio. Particle sizes were measured and shown in Table 1.

Nanoparticles of Comparative Polymers $C_{18}$-PEOXABP200 and $C_{18}$-PEOXABP100 and Paclitaxel With the same procedure, two comparative polymers having different monomer/initiator ratios, $C_{18}$-PEOXABP200 and $C_{18}$-PEOXABP100, were used to produce comparative aggregates at two different weight ratios of polymer:drug, 5:1 and 7:1. Aggregate sizes were measured, and data are shown in Table 1.

Nanoparticle Measurement

The size of various polymers, polymer-only aggregates, as well as drug-induced polymer aggregates was measured by a dynamic light scattering method using a Malvern Zetasizer Nano-ZS Zen3600 particle size analyzer (Malvern Panalytical Inc., Westborough, MA).

As shown in Table 1, a polymer having a monomer to initiator molar ratio of 100:1 or higher yielded polymer-drug aggregates over 100 nm in size, both at 5:1 and 7:1 polymer: drug weight ratios. Polymer-drug aggregates produced with a polymer having a monomer to initiator molar ratio at 80:1, 60:1, 50:1 or 20:1 yielded aggregate having particle sizes in a range of from about 70 to 100 nm.

D(v,0.9) value (also known as $D_{90}$) can be obtained using, for example, a Malvern Zetasizer Nano-ZS Zen3600 particle size analyzer. The $D_{90}$ value is that where 90% of particles have a size (in diameter) below, smaller than or lower than that value. $D_{90}$ values for polymer-drug aggregates prepared from $C_{18}$-PEOXABP100 (comparative) and $C_{18}$-PEOXABP60 (invention) are shown in Table 1.

TABLE 1

Particle size of polymer-drug aggregates.

| Polymer | Polymer/Drug Ratio | Aggregate Size (d, nm) | $D_{90}$ |
|---|---|---|---|
| $C_{18}$-PEOXABP200 (Comparative) | 5 to 1 | >200 | — |
| $C_{18}$-PEOXABP100 (Comparative) | 5 to 1 | 159 | — |
| $C_{18}$-PEOXABP100 (Comparative) | 7 to 1 | 120 | 209 |
| $C_{18}$-PEOXABP80 | 7 to 1 | 94 | — |
| $C_{18}$-PEOXABP60 | 7 to 1 | 99 | 173 |
| $C_{18}$-PEOXABP50 | 7 to 1 | 89 | — |
| $C_{18}$-PEOXABP20 | 7 to 1 | 75 | — |

Measurement of Filtration Rate

Polymer-drug aggregates prepared above were measured for $R_f$ according to the following procedure.

Each of the polymer-drug aggregate samples was prepared and dissolved in water as described herein to a same final concentration. A final paclitaxel concentration of 3 mg/mL was used for samples with data presented in Table 2.

A starting volume ($V_0$) of each of samples was loaded into a sterile syringe. A single use 25 mm sterile 0.22 µm syringe filter assembly (Pall Corp., Ann Arbor, MI) was affixed to the syringe. A $V_0$ volume of 9 ml was used for each sample. For a 25 mm filter, starting volume can be in a range of from 9 to 10 ml.

Each sample was then made to pass through the 0.22 µm filter by depressing the plunger of the syringe with a constant thumb pressure until all of the sample volume passed through the filter or the plunger no longer moved forward under the same pressure.

Sample volume remaining in the syringe ($V_1$) was recorded. The filtered volume ($V_f$) or filtrate was calculated based on the formula, $V_f = V_0 - V_1$. Alternatively, the sample that passed through the filter can be collected and $V_f$ was measured as the volume of filtrate or collected, filtered sample.

$R_f$ for each sample was calculated based on the formula, $R_f = V_f/V_0$.

For polymer-drug aggregates prepared from $C_{18}$-PEOXABP60 and paclitaxel, all 9 ml passed through the filter, $V_f = 9$, resulting in $R_f = 1$ or 100%.

A comparative polymer-drug aggregate was prepared from $C_{18}$-PEOXABP100 and paclitaxel. Only 4.4 ml passed through the filter. Hence, $V_f = 4.4$ resulting in $R_f = 4.4/9$ or 0.489 or 48.9%. Data are shown in Table 2.

TABLE 2

Filtration rate of polymer-drug aggregates.

| | Example | Comparative Sample |
|---|---|---|
| Polymer | $C_{18}$-PEOXABP60 | $C_{18}$-PEOXABP100 |
| Polymer:Drug Ratio | 7:1 | 7:1 |
| Filter Pore Size | 0.22 µm | 0.22 µm |
| Filtration Rate ($R_f$) | 100% | 48.9% |

Activity Testing

Metabolism in viable cells produces, "reducing equivalents," such as, NADH or NADPH. Such reducing compounds pass electrons to an intermediate electron transfer reagent that can reduce the tetrazolium product, MTS (Promega), into an aqueous, soluble formazan product, which is colored. At death, cells rapidly lose the ability to reduce tetrazolium products. The production of the colored formazan product, therefore, is proportional to the number of viable cells in culture.

CellTiter 96® AQ$_{ueous}$ products (Promega, Madison, WI) are materials and methods for conducting MTS assays for determining the number of viable cells in culture. A single reagent added directly to the assay wells at a recommended ratio of 20 µl reagent to 100 µl of culture medium was used. Cells were incubated 1-4 hours at 37° C. and then absorbance was measured at 490 nm.

Toxicity and Efficacy of Nanoencapsulated Paclitaxel/ABP60 (FIB-007)

As previously described, nanoencapsulated paclitaxel was prepared using $C_{18}$-PEOXABP60 polymer with a polymer to paclitaxel ratio of 7:1. That preparation, given the designation FID-007, was compared to TAXOL and ABRAXANE in cytotoxicity studies with normal human dermal fibroblast cell lines and various cancer cell lines, and in in vivo studies of toxicity (maximum tolerated dose, MTD) and inhibition of tumor growth in three mouse xenograft models.

In Vitro Activity of FID-007

FID-007 was tested with TAXOL and ABRAXANE on normal human fibroblast cells and on various cancer cell lines in in vitro cytotoxicity experiments. While FID-007 inhibits the proliferation of a range of human cancer cell lines in vitro including lines originating from breast, ovarian and lung cancer cells, FID-007 exhibited lower toxicity on normal cells, similar to the levels observed with TAXOL and ABRAXANE (FIG. 15). Overall, FID-007 was 10 times less toxic to normal cells than to tumor cells, exhibiting a very high $EC_{50}$ (concentration of drug that yields a half maximal response), greater than 100 µM. FID-007 was active in a 72 h toxicity assay in human lung cancer cell line A549 with an $EC_{50}$ of 2.8 ng/mL (FIG. 16). FID-007 was cytotoxic to MDA-MB-231 (triple negative breast cancer cells) with an $EC_{50}$ of 4.9 ng/mL (FIG. 17). FID-007 was cytotoxic to OV-90 (ovarian cancer cells) with an $EC_{50}$ of 5.0 ng/mL (FIG. 18). With all three cancer cell lines, FID-007 cytotoxicity was comparable to that of TAXOL and ABRAXANE.

In Vivo Activity of FID-007

A series of experiments was performed to determine in vivo tolerability, activity and basic pharmacokinetics of FID-007 administered intravenously (IV) in mice, as compared to TAXOL and ABRAXANE. FID-007 was well tolerated up to 150 mg/kg daily dosing. To confirm antineoplastic activity, FID-007 was administered IV daily at well-tolerated doses to mice in three different mouse xenograft models (including lung, ovarian and breast cancers). In general, FID-007 was better tolerated in mouse xenograft models than standard cytotoxic agents that have similar targets, such as, TAXOL and ABRAXANE, and selectively inhibited the growth of tumors.

Half-life of FID-007 in mice was determined, using an optimized HPLC method, to be approximately 9.3 hours. Liver and spleen, followed by blood were the organs with the highest concentration of FID-007 at 1 hour. The PK profiles of FID-007, TAXOL and ABRAXANE are shown in FIG. 19.

The single dose MTD of FID-007 was compared to that of TAXOL and ABRAXANE in a study wherein various doses of the drugs were administered through the tail vein of healthy CD-1 mice and SCID (immune deficient) mice over the course of several weeks. Control mice were administered saline. The single dose MTD for TAXOL, ABRAXANE, and FID-007 on CD-1 mice was found to be 20 mg/kg, 240 mg/kg, and 175 mg/kg, respectively. No major side effects were observed in all the mice that survived. However, weight gain was observed in all the treatment groups of ABRAXANE and FID-007 as compared to the control groups (treated with saline). ABRAXANE at 120 mg/kg and above caused a dose-dependent increase in weight. The same was observed with FID-007 at closes of 150 mg/kg and higher.

The multiple dose MTD of FID-007 was determined similarly by administering FID-007 (100 and 150 mg/kg) to healthy CD-1 and SCID mice (10 weeks, females) via the tail vein at day 0, day 3 and day 6. Animals were monitored twice per day and weighed every 3 days. The multiple dose MTD for FID-007 in CD-1 mice was determined to be 100 mg/kg and was 30 mg/kg in SCID mice with some side effects immediately after injection. The FID-007 multiple dose groups did not have excessive weight gain as compared to the control group.

The in vivo efficacy of FID-007 in inhibiting tumor growth was compared to that of TAXOL and ABRAXANE in tumor xenograft mouse models of human lung, breast and ovarian cancer. Sixty female and male SCID mice (6-8 weeks, 20-26 g, Charles River, 40 female mice for breast and ovarian cancer, 20 male mice for lung cancer) were injected on each side of the torso (left and right) with 0.1 mL of suspension of lung A549, breast MDA-MB-231 or ovarian OV90 cells in serum-free medium. Cells were cultured previously in a humidified incubator (37° C., 5% $CO_2$, 95% air). Doses of $3\times10^6$ (A549), $10^7$ (MDA-MB-231) and $5\times10^6$ (OV-90) cells were used per mouse tumor. The tumors were allowed to grow for 7 to 9 days before treatment started, and all tumor volume measurements were obtained using a digital caliper (VWR Inc.). The tumor volumes were calculated by the formula $(W^2\times L)/2$, where W is the maximum tumor width and L is the maximum tumor length. Tumor and body weight measurements were obtained on the same day prior to the first treatment, then every three days. Day 0 was designated as the first day of treatment. On day 0, the animals that developed tumors were divided randomly into five groups [about 4 mice (8 tumors) per group], with each treatment group representing a wide range of tumor sizes. Volumes of OV-90 xenograft tumors are shown in FIG. 22.

ABRAXANE (80 mg/kg), FID-007 (20 mg/kg), TAXOL (20 mg/kg) and $C_{18}$-ABP60 polymer starting material, designated as NanoCarrier 001-B (20 mg/kg), were prepared fresh for each injection. Saline was used as a vehicle control. The drugs or saline were administered through tail vein injection every three days. Drug doses were chosen to be equitoxic for all treatment groups based on previously determined single and multiple dose MTD's. Lung, breast and ovarian cancer groups each received a total of four injections. Injection volume for control, ABRAXANE and FID-007 was 0.1 mL per injection throughout the entire study. Due to viscosity of the TAXOL formulation, 0.2 mL per injection were administered for the 20 mg/kg dose. Average body weight and tumor volume measurements were calculated by averaging across the animals within the same group. The mice were euthanized with isoflurane 21 days from the last treatment for lung cancer and ovarian cancer, and 10 days for breast cancer. Blood and isolated serum, as well as tumor tissues and liver were collected and stored at −80° C.

For the lung cancer (A549) xenograft group, overall, no deaths occurred in any of the treatment groups. Probably due to the toxicity of TAXOL, heavy breathing and inactivity were observed in the first 30 minutes post treatment in a couple of mice. Average body weight and tumor volume measurements were calculated by averaging across the animals within the same group. The overall average body weight gains for saline control, TAXOL, FID-007 and Nano vehicle control were 6.05%, 5.87%, 6.38% and 12.3%, respectively. However, all mice in the ABRAXANE group developed neurotoxicity and lost >20% weight. Those mice were sacrificed at 13 days. Tumor volume increased by 1827 $mm^3$ for the saline control group and 1311 $mm^3$ for the NanoCarrier-001B vehicle control group, and by 305.8 $mm^3$ for the TAXOL group. However, FID-007 groups had a reduction in tumor volume by 39.7 $mm^3$ (FIG. 20). FIG. 21 and FIG. 23 show representative images of tumors of the treatment groups.

For the breast cancer (MDA-MB-231) xenograft group, no deaths occurred in any of the treatment groups. Possibly due to the toxicity of TAXOL, heavy breathing and inactivity were observed in the first 30 minutes post treatment. In the ABRAXANE group, all mice showed side effects of weak hind legs and 20% body weight loss after three treatments, leading to a decision to stop the $4^{th}$ treatment for that group. Average body weight and tumor volume measurements were calculated by averaging across the animals within the same group. The overall average body weight gains for saline, TAXOL, FID-007 and NanoCarrier-001B were 3.76%. 0.46%, 1.8%, and 4.2%, respectively. For the ABRAXANE group, average body weight loss was 7.66%. Tumor volume increased by 328.6 $mm^3$ and 458.8 $mm^3$ in the saline and NanoCarrier-001B groups, respectively. In the FID-007, TAXOL and ABRAXANE groups, tumor volumes decreased by 108.7 $mm^3$, 75.5 $mm^3$ and 70.2 $mm^3$, respectively. Tumor volume observations are shown in FIG. 23.

For the ovarian cancer (OV-90) xenograft group, the TAXOL treatment group showed some toxicity with heavy breathing and inactivity observed in the first 30 minutes post treatment in two mice. The average body weight gain was 3.23%, 17.1%, 13.5%, 15.4% and 2.24% in the saline control, TAXOL, ABRAXANE, FID-007 and NanoCarrier-001B control groups, respectively. Tumor volume increased by 652.7 $mm^3$, 271.9 $mm^3$ and 9.1 $mm^3$ in saline control, NanoCarrier-001B control and TAXOL groups, respectively, while there was a decrease in tumor volume in the FID-007 group by 93.1 $mm^3$ and in the ABRAXANE group (80 mg/kg) by 72.4 $mm^3$.

FID-007 demonstrated in vitro cytotoxicity to lung, breast and ovarian cell lines similar to the established antineoplastic drugs TAXOL and ABRAXANE, while maintaining a low level of toxicity to normal cells. The in vivo efficacy of FID-007 in inhibiting tumor growth and reducing tumor mass was as good as or significantly better than the two approved drugs in mouse xenograft models of human lung, breast, and ovarian cancers.

All references cited herein are herein incorporated by reference in entirety.

It will be appreciated that various changes and modifications can be made to the teachings herein without departing from the spirit and scope of the disclosure.

What is claimed is:

1. Aggregates comprising:
   a) a polymer comprising a polyoxazoline comprising at least one first terminal group modified with a hydrophobic moiety, wherein said polyoxazoline further comprises a linear portion, a branched portion or both, said branched portion comprises a symmetrically branched polymer, an asymmetrically branched polymer or a combination thereof; and said polyoxazoline comprises a molar ratio of monomer to initiator of 55:1, 56:1, 57:1, 58:1, 59:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1 or 80:1, and b) a taxane, wherein said aggregates comprise a weight ratio of said polymer to said taxane of 6:1 to 8:1; and are from 70 nm to 90 nm in size; and said polyoxazoline comprises a second terminal group comprising a functional group modified by an ethylenediamine (EDA), or an EDA derivative, at a ratio of said second terminal group to said EDA of 1:10.

2. The aggregates of claim 1, wherein said initiator comprises a hydrophobic electrophilic molecule.

3. The aggregates of claim 1, wherein said initiator comprises a hydrocarbon.

4. The aggregates of claim 1, wherein said initiator comprises an aliphatic hydrocarbon, an aromatic hydrocarbon or a combination of both.

5. The aggregates of claim 1, wherein said initiator comprises a halide functional group.

6. The aggregates of claim 1, wherein said initiator comprises an alkyl halide, an aralkyl halide, an acyl halide or combination thereof.

7. The aggregates of claim 3, wherein said hydrocarbon comprises from 1 to about 22 carbons, which may be saturated or unsaturated.

8. The aggregates of claim 1, wherein said initiator comprises methyl iodide, methyl bromide, methyl chloride, ethyl iodide, ethyl bromide, ethyl chloride, 1-iodopropane, 1-bromopropane, 1-chloropropane, 1-iodobutane, 1-bromobutane, 1-chlorobutane, 1-iodopentane, 1-bromopentane, 1-chloropentane, 1-iodohexane, 1-bromohexane, 1-chlorohexane, 1-iodododecane, 1-bromododecane, 1-chlorododecane, 1-iodooctadodecane, 1-bromooctadodecane, 1-chlorooctadodecane, benzyl iodide, benzyl bromide, benzyl chloride, allyl bromide, acyl iodide, acyl bromide, acyl chloride, benzoyl bromide, benzoyl chloride or a combination thereof.

9. The aggregates of claim 1, wherein said initiator comprises a tosyl group.

10. The aggregates of claim 1, wherein said EDA derivative comprises diethylenetriamine, triethylenetetramine, tetraethylenepentamine, pentaethylenehexamine, polyethylene amine or tetramethylethylenediamine.

11. The aggregates of claim 1, wherein said taxane is associated with said at least one first terminal group.

12. The aggregates of claim 1, wherein said polyoxazoline comprises poly(2-oxazoline), poly(2-substituted oxazoline) or a combination thereof.

13. The aggregates of claim 1, wherein said polyoxazoline comprises poly(2-methyloxazoline), poly(2-ethyloxazoline), poly(2-propyloxazoline), poly(2-butyloxazoline) or a combination thereof.

14. The aggregates of claim 1, wherein said taxane comprises paclitaxel, docetaxel or a combination thereof.

15. The aggregates of claim 1, wherein said polymer to said taxane ratio is 7:1.

16. A pharmaceutical composition for treating a patient with a disease treatable with taxane comprising the aggregates of claim 1 and a pharmaceutically effective diluent, carrier or excipient.

17. The pharmaceutical composition of claim 16, wherein said disease comprises a breast cancer, an ovarian cancer, a lung cancer, NSCLC (Non-Small Cell Lung Cancer), a colon cancer, a gastric cancer, a melanoma, a head and neck cancer, a pancreatic cancer or a combination thereof.

18. The pharmaceutical composition of claim 16, wherein said disease comprises a head and neck cancer.

19. A method for treating a patient with a disease treatable with taxane comprising administering to said patient the pharmaceutical composition of claim 16.

20. The method of claim 19, wherein said aggregates comprise a monomer to initiator ratio is 60:1 and said polymer to said taxane ratio is 7:1.

* * * * *